(12) United States Patent
Bowman et al.

(10) Patent No.: US 12,239,389 B2
(45) Date of Patent: Mar. 4, 2025

(54) SYSTEMS AND METHODS FOR USING PHOTOGRAMMETRY TO CREATE PATIENT-SPECIFIC GUIDES FOR ORTHOPEDIC SURGERY

(71) Applicant: MicroPort Orthopedics Holdings Inc., Arlington, TN (US)

(72) Inventors: Fred W. Bowman, Germantown, TN (US); C. Brian McDaniel, Sr., Arlington, TN (US); Paul S. Bryant, Collierville, TN (US); Brian R. Harris, Jr., Cordova, TN (US)

(73) Assignee: MicroPort Orthopedics Holdings Inc., Arlington, TN (US)

(*) Notice: Subject to any disclaimer, the term of this patent is extended or adjusted under 35 U.S.C. 154(b) by 353 days.

(21) Appl. No.: 17/813,378

(22) Filed: Jul. 19, 2022

(65) Prior Publication Data
US 2023/0027518 A1    Jan. 26, 2023

Related U.S. Application Data

(60) Provisional application No. 63/223,844, filed on Jul. 20, 2021.

(51) Int. Cl.
*A61B 34/20* (2016.01)
*A61B 90/00* (2016.01)

(52) U.S. Cl.
CPC .............. *A61B 34/20* (2016.02); *A61B 90/37* (2016.02); *A61B 2034/2065* (2016.02); *A61B 2090/376* (2016.02); *G06T 2207/10116* (2013.01)

(58) Field of Classification Search
CPC . A61B 34/20; A61B 90/37; A61B 2034/2065; A61B 2090/376; G06T 2207/10116
(Continued)

(56) References Cited

U.S. PATENT DOCUMENTS

| 6,891,518 B2 | 5/2005 | Sauer et al. |
| 6,919,867 B2 | 7/2005 | Sauer |

(Continued)

FOREIGN PATENT DOCUMENTS

| CN | 102599960 | 8/2015 |
| CN | 105266897 | 1/2016 |

(Continued)

OTHER PUBLICATIONS

Thomas, Shane, International Search Report, US Receiving Office, mailed Oct. 11, 2022.
(Continued)

*Primary Examiner* — William D Titcomb
(74) *Attorney, Agent, or Firm* — Robert J. Hornung

(57) ABSTRACT

Systems and methods for generating patient-specific surgical guides comprising: capturing a first and second images of an orthopedic element in different reference frames using a radiographic imaging technique, detecting spatial data defining anatomical landmarks on or in the orthopedic element using a neural network, applying a mask to the orthopedic element defined by an anatomical landmark, projecting the spatial data from the first image and the second image to define volume data, applying the neural network to the volume data to generate a reconstructed three-dimensional ("3D") model of the orthopedic element; and calculating dimensions for a patient-specific surgical guide configured to abut the orthopedic element.

8 Claims, 13 Drawing Sheets

(58) Field of Classification Search
USPC .......................................................... 382/128
See application file for complete search history.

(56) References Cited

U.S. PATENT DOCUMENTS

| | | | |
|---|---|---|---|
| 7,511,736 | B2 | 3/2009 | Benton |
| 7,618,451 | B2 | 11/2009 | Berez et al. |
| 7,771,436 | B2 | 8/2010 | Moctezuma De La Barrera et al. |
| 7,774,044 | B2 | 8/2010 | Sauer et al. |
| 7,806,896 | B1 | 10/2010 | Bonutti |
| 8,485,038 | B2 | 7/2013 | Sengupta et al. |
| 8,543,338 | B2 | 9/2013 | Bronstein et al. |
| 8,634,897 | B2 | 1/2014 | Simon et al. |
| 8,657,809 | B2 | 2/2014 | Schoepp |
| 8,842,893 | B2 | 9/2014 | Teichman et al. |
| 8,963,957 | B2 | 2/2015 | Skarulis |
| 9,089,342 | B2 | 7/2015 | Carroll et al. |
| 9,439,622 | B2 | 9/2016 | Case et al. |
| 9,547,940 | B1 | 1/2017 | Sun et al. |
| 9,610,056 | B2 | 4/2017 | Lavallee et al. |
| 9,681,925 | B2 | 7/2017 | Azar et al. |
| 9,901,463 | B2 | 2/2018 | Mahfouz |
| 10,166,109 | B2 | 1/2019 | Ferko |
| 10,258,426 | B2 | 4/2019 | Silva et al. |
| 10,510,155 | B1 | 12/2019 | Islam et al. |
| 10,722,310 | B2 | 7/2020 | Luby |
| 10,940,021 | B2 | 3/2021 | Mahfouz |
| 11,076,872 | B2 | 8/2021 | Wilkinson |
| 11,423,603 | B2 | 8/2022 | Sutton et al. |
| 11,439,469 | B2 | 9/2022 | Poltaretskyi et al. |
| 11,517,334 | B1* | 12/2022 | Jaramaz ................ A61B 34/20 |
| 11,553,969 | B1* | 1/2023 | Lang ................. G06T 7/0012 |
| 11,589,949 | B1* | 2/2023 | Mills .................... A61B 5/0037 |
| 11,612,436 | B2* | 3/2023 | McAfee ............ A61B 17/7011 |
| | | | 606/130 |
| 11,998,278 | B1* | 6/2024 | Dumpe ................. A61B 90/37 |
| 2008/0114370 | A1 | 5/2008 | Schoenefeld |
| 2008/0167550 | A1 | 7/2008 | Weiser et al. |
| 2009/0306679 | A1 | 12/2009 | Murphy |
| 2011/0071533 | A1 | 3/2011 | Metzger et al. |
| 2011/0236868 | A1 | 9/2011 | Ran et al. |
| 2012/0065640 | A1 | 3/2012 | Metzger et al. |
| 2013/0060146 | A1 | 3/2013 | Yang et al. |
| 2013/0117377 | A1 | 5/2013 | Miller |
| 2013/0310838 | A1 | 11/2013 | Kurtz |
| 2014/0013566 | A1 | 1/2014 | MacDonald |
| 2014/0013565 | A1 | 9/2014 | MacDonald et al. |
| 2016/0008143 | A1 | 1/2016 | Mahfouz |
| 2016/0026253 | A1 | 1/2016 | Bradski et al. |
| 2016/0228193 | A1 | 8/2016 | Moctezuma de la Barrera et al. |
| 2017/0367766 | A1* | 12/2017 | Mahfouz ................ A61B 17/15 |
| 2018/0168740 | A1 | 6/2018 | Ryan et al. |
| 2018/0177600 | A1 | 6/2018 | Karlsson et al. |
| 2018/0185100 | A1 | 7/2018 | Weinstein et al. |
| 2019/0008532 | A1* | 1/2019 | Fitz ........................ G06F 30/00 |
| 2019/0029757 | A1* | 1/2019 | Roh ........................ A61B 34/20 |
| 2019/0262078 | A1* | 8/2019 | Lang ................. A61B 17/1775 |
| 2019/0380792 | A1* | 12/2019 | Poltaretskyi ........... A61B 17/15 |
| 2020/0138522 | A1 | 5/2020 | Tikka |
| 2020/0375666 | A1 | 12/2020 | Murphy |
| 2020/0405399 | A1* | 12/2020 | Steinberg .................. G06T 7/33 |
| 2021/0192759 | A1* | 6/2021 | Lang ................. A61B 90/98 |
| 2021/0282858 | A1* | 9/2021 | Hill ........................ A61B 34/20 |
| 2022/0039868 | A1* | 2/2022 | Chaoui ................ G06T 7/0012 |
| 2022/0096245 | A1 | 3/2022 | Sun et al. |
| 2022/0338938 | A1* | 10/2022 | Walen ................ A61B 17/1624 |
| 2023/0019543 | A1* | 1/2023 | Nikou .................... A61B 8/461 |
| 2023/0087709 | A1* | 3/2023 | Karduss ................ A61B 34/10 |
| 2023/0149116 | A1* | 5/2023 | Stauffer ................. G16H 20/40 |
| | | | 606/102 |
| 2023/0157756 | A1* | 5/2023 | Simoes ................ A61B 5/4576 |
| | | | 703/11 |
| 2023/0404684 | A1* | 12/2023 | Jaramaz ................ A61B 34/30 |

FOREIGN PATENT DOCUMENTS

| | | |
|---|---|---|
| WO | 2012154534 | 11/2012 |
| WO | 2014120909 | 8/2014 |
| WO | 2016078919 | 5/2016 |
| WO | 2017066373 | 4/2017 |
| WO | 2018078017 | 4/2017 |
| WO | 2017200444 | 11/2017 |
| WO | 2021245093 | 12/2021 |

OTHER PUBLICATIONS

Thomas, Shane, Written Opinion of the International Searching Authority, US Receiving Office, mailed Oct. 11, 2022.
Vincent Masse, Raju S. & Ghate, "Using Standard X-ray Images to Create 3D Digital Bone Models and Patient-Matched Guides for Aiding Implant Positioning and Sizing in Total Knee Arthroplasty," Computer Assisted Surgery, Mar. 15, 2021, 36:1, 31-40.
Tanguy Roudaut, Partial European Search Report and Written Opinion for EP app, No. 22182089, Feb. 23, 2023, Munich, Germany.
Thomas, Shane, International Search Report for PCT/US22/77111, Dec. 28, 2022, USPTO as ISA, Alexandria, Virginia, USA.
Thomas, Shane, Written Opinion of the International Searching Authority for PCT/US22/77111, Dec. 28, 2022, USPTO as ISA, Alexandria, Virginia, USA.
Matos, Taina, International Search Report for PCT/US22/77133, Dec. 8, 2022, USPTO as ISA, Alexandria, Virginia, USA.
Matos, Taina, Written Opinion of the International Searching Authority for PCT/US22/77133, Dec. 8, 2022, USPTO as ISA, Alexandria, Virginia, USA.
Thomas, Shane, International Search Report for PCT/US22/73868, Oct. 11, 2022, USPTO as ISA, Alexandria, Virginia, USA.
Thomas, Shane, Written Opinion of the International Searching Authority for PCT/US22/73868, Oct. 11, 2022, USPTO as ISA, Alexandria, Virginia, USA.
S.Hosseinian, H. Arefi, Photogrammetry in 3D Modelling of Human Bone Structures From Radiographs, International Archives of the Photogrammetry, Remote Sensing and Spatial Information Sciences, vol. XLII-2/W4, 2017 2nd International ISPRS Workshop on PSBB, May 15-17, 2017, Moscow, Russia.
Fausto Milletari, et. al., V-Net: Fully Convolutional Neural Networks for Volumetric Medical Image Segmentation., arXiv:1606.04797v1 [cs.CV] Jun. 15, 2016.
J. C. K. Chow, Modelling Errors in X-Ray Fluoroscopic Imaging Systems Using Photogrammetric Bundle Adjustment With a Data-Driven Self-Calibration Approach, The International Archives of the Photogrammetry, Remote Sensing and Spatial Information Sciences, vol. XLII-1, 2018 ISPRS TC I Mid-term Symposium "Innovative Sensing—From Sensors to Methods and Applications", Oct. 10-12, 2018, Karlsruhe, Germany.
Dr. F. G. Lippert III, M.D., An Analytical Approach to X-Ray Photogrammetry, Photogrammetric Engineering and Remote Sensing, vol. 43, No. 12, Dec. 1977, pp. 1503-1510. S. A. Veress, Ds.C., University of Washington, Seattle, WA 98195.
Avi-Ben-Cohen, Retinal layers segmentation using Fully Convolutional Network in OCT images.
Yoni Kasten, End-To-End Convolutional Neural Network for 3D Reconstruction of Knee Bones From Bi-Planar X-Ray Images, arXiv:2004.00871v2 [eess.IV] Aug. 12, 2020.
Ilya Kovler, Haptic computer-assisted patient-specific preoperative planning for orthopedic fractures surgery, Int J CARS DOI 10.1007/s11548-015-1162-9.
Sandor A. Veress, X-Ray Photogrammetry, State of the Art, University of Washington Seattle, WA 98195 United States IPRS Commission V.
Zimmer Biomet, Image Acquisition Protocol for X-PSI™ Knee System, 2018.
Yilmaz, Ozgun, Supplementary European Search Report (art. 153(7) EPC) and European Search Opinion, Oct. 4, 2024, Munich, Germany.

(56) References Cited

OTHER PUBLICATIONS

A Uneri et. al., "Known-composent 3D-2D registration for quality assurance of spine surgery pedicle screw placement," Physics in Medicen & Biology, 2015, vol. 50, pp. 8007-8024, United Kingdom.

* cited by examiner

SYSTEMS AND METHODS FOR USING PHOTOGRAMMETRY TO CREATE PATIENT-SPECIFIC GUIDES FOR ORTHOPEDIC SURGERY

REFERENCE TO RELATED APPLICATION

This application claims the benefit of U.S. Provisional Application No. 63/223,844 filed on Jul. 20, 2021. The disclosure of this related application is hereby incorporated into this disclosure in its entirety.

BACKGROUND OF THE INVENTION

1. Technical Field

The present disclosure relates generally to the field of orthopedic joint replacement surgeries and more particularly to using photogrammetry and three-dimensional ("3D") reconstruction techniques to aid surgeons and technicians in planning and executing orthopedic surgeries.

2. Related Art

An emerging objective of joint replacement surgeries is to restore the natural alignment and rotational axis or axes of the pre-diseased joint. However, this objective can be difficult to achieve in practice, because joints comprise not just the articulating bones but also ancillary supporting bones and a variety of soft tissue, including cartilage, ligaments, muscle, and tendons. In the past, surgeons avoided restoring natural alignment altogether, or estimated alignment angles and other dimensions based on averages derived from a sample of the population. However, these averages often failed to account for natural variation in the anatomy of a specific patient, particularly when the patient suffered from chronic bone deforming diseases like osteoarthritis.

In an attempt to address this, some care providers started using computed tomography ("CT") scans and magnetic resonance imaging ("MRI") techniques to survey patient's internal anatomy to help plan orthopedic surgeries. Data from these CT scans and MRIs have even been used to create three-dimensional ("3D") models in digital form. These models can be sent to professionals to design and produce patient-specific instruments (such as custom surgical resection guides) for said surgery. Additive manufacturing techniques (e.g., 3D printing) and other conventional production techniques can be used to construct physical instruments that fit the patient's specific anatomy.

However, obtaining CT scans and MRIs can be complex, time consuming, and expensive. CT scans also tend to expose patients to higher levels of radiation per session than the patient might otherwise undergo using other non-invasive imaging techniques such as traditional radiography or ultrasounds. Moreover, scheduling considerations sometimes place the surveying CT scans or MRIs a month or more before the actual surgery. This delay can be exacerbated by the trend of gradually moving orthopedic surgical procedures to outpatient ambulatory surgical centers ("ASCs"). ASCs tend to be smaller facilities that often lack expensive on-site CT scanners and MRI machines. This often compels patients to schedule surveying appointments at hospitals.

Increased time between the surveying appointment and the surgery increases the risk that the patient's boney and soft tissue anatomy will further deteriorate or change under normal use or by progression of a disease. Further deterioration not only causes the patient additional discomfort, but it can also negatively affect the surveying data's usefulness to the surgical team. This can be especially problematic for patient-specific guides created from outdated data and for surgical techniques that seek to restore range of motion based on the natural alignment of pre-diseased joints. Furthermore, increased time between the preoperative surveying appointment and the surgery increases the likelihood that extrinsic events will negatively affect the data. For example, an accident that dislocates or breaks a bone in the planned surgical area usually undermines the usefulness of the prior surveying data. Such risks may be higher in especially active or in especially frail individuals.

Additionally, not all patients have access to CT scans or MRIs for creating patient-specific instruments. This can be due in part to the amount of time needed to acquire the data, send the data to a medical device design specialist, produce a 3D model of the desired anatomy, create a patient-specific instrument design based upon the data or model, produce the patient-specific instrument, track and ship said patient-specific instrument to the surgical center, and sterilize said instrument prior to the procedure. Lack of availability can also be a function of the patient's medical insurance and type of disease.

Therefore, these techniques, coupled with the problems and availability of accurate preoperative data, can jeopardize the accurate alignment of the artificial joint line with the natural pre-diseased joint line. Repeated studies have shown that artificial joints that change the natural rotational axes of pre-diseased joints tend to contribute to poor function, pre-mature implant wear, and patient dissatisfaction.

SUMMARY OF THE INVENTION

Accordingly, there is a long felt but unresolved need to augment preoperative and intraoperative imaging technologies to accurately model the operative joint, including bone structure, bone loss, soft tissue, and other physiology when planning and executing orthopedic surgeries.

The problems of limited access to conventional preoperative CT and MRI imaging techniques, data accuracy due to bone and cartilage deterioration between the time of preoperative imaging and surgical procedure, and the limitations of determining the natural joint lines of pre-diseased joints using currently available intraoperative tools and techniques can be mitigated by exemplary systems and methods for generating patient-specific surgical drill or resection guides comprising: using a deep learning network to identify and model an orthopedic element and using the deep learning network to calculate dimensions for a patient-specific surgical guide configured to abut the orthopedic element from an input of at least two separate two-dimensional ("2D") input images of a subject orthopedic element, wherein the first image of the at least two separate 2D input images is captured from a first transverse position, and wherein the second image of the at least two separate 2D input images is captured from a second transverse position offset from the first transverse position by an offset angle.

Radiographs allow for in-vivo analysis that can account for external summation of passive soft tissue structures and dynamic forces occurring around the knee, including the effect of ligamentous restraints, load-bearing forces, and muscle activity.

Creating patient-specific surgical plans and instruments typically uses data from the cartilage and bony anatomy, such as the contour of a knee, but data from the soft tissue structures can also be used.

BRIEF DESCRIPTION OF THE DRAWINGS

The foregoing will be apparent from the following more particular description of exemplary embodiments of the disclosure, as illustrated in the accompanying drawings. The drawings are not necessarily to scale, with emphasis instead being placed upon illustrating the disclosed embodiments.

DETAILED DESCRIPTION OF THE PREFERRED EMBODIMENTS

Figure 1:
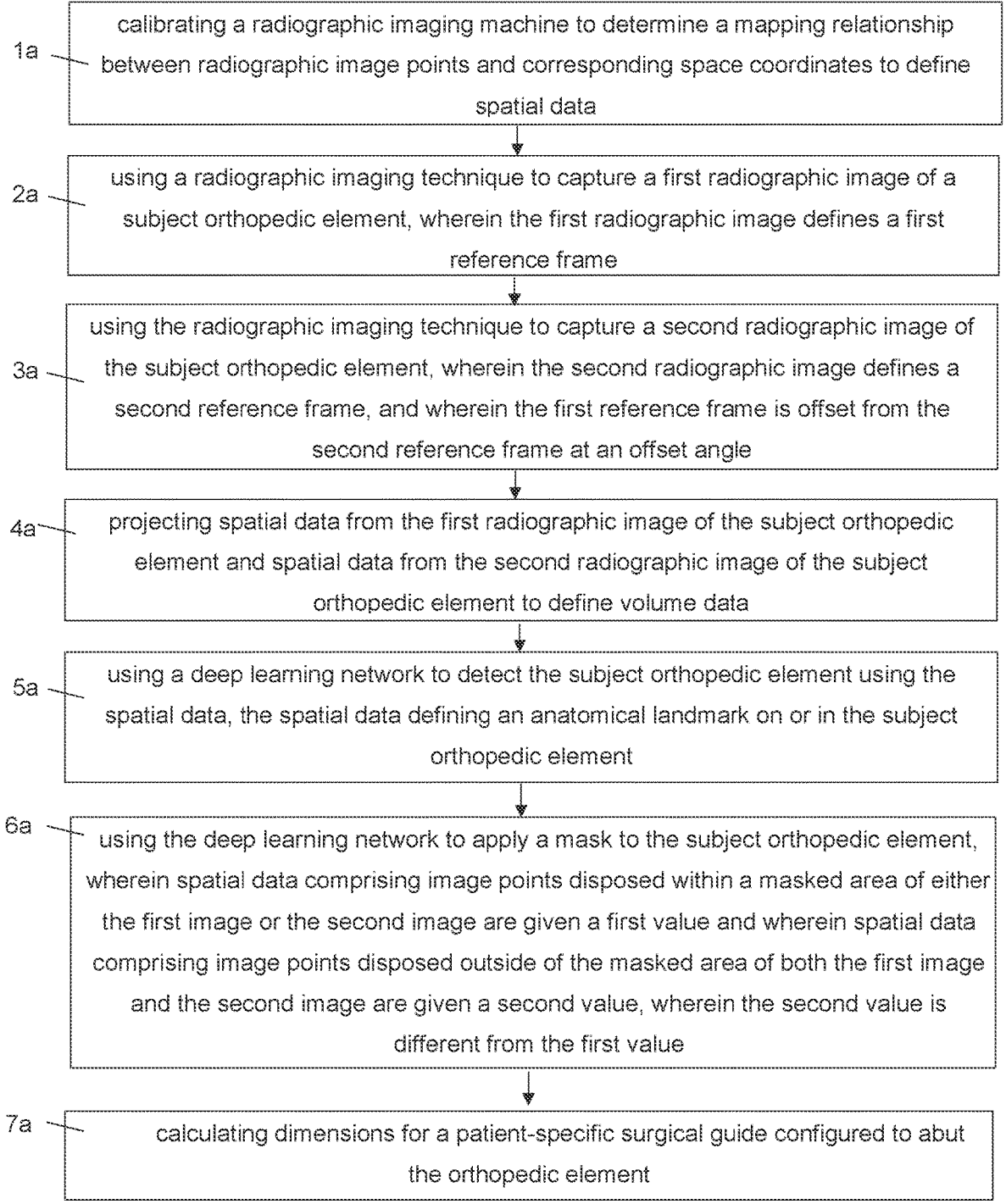
FIG. 1 is a flow chart illustrating steps of an exemplary method.

The following detailed description of the preferred embodiments is presented only for illustrative and descriptive purposes and is not intended to be exhaustive or to limit the scope and spirit of the invention. The embodiments were selected and described to best explain the principles of the invention and its practical application. One of ordinary skill in the art will recognize that many variations can be made to the invention disclosed in this specification without departing from the scope and spirit of the invention.

Similar reference characters indicate corresponding parts throughout the several views unless otherwise stated. Although the drawings represent embodiments of various features and components according to the present disclosure, the drawings are not necessarily to scale and certain features may be exaggerated to better illustrate embodiments of the present disclosure, and such exemplifications are not to be construed as limiting the scope of the present disclosure.

Except as otherwise expressly stated herein, the following rules of interpretation apply to this specification: (a) all words used herein shall be construed to be of such gender or number (singular or plural) as such circumstances require; (b) the singular terms "a," "an," and "the," as used in the specification and the appended claims include plural references unless the context clearly dictates otherwise; (c) the antecedent term "about" applied to a recited range or value denotes an approximation with the deviation in the range or values known or expected in the art from the measurements; (d) the words, "herein," "hereby," "hereto," "hereinbefore," and "hereinafter," and words of similar import, refer to this specification in its entirety and not to any particular paragraph, claim, or other subdivision, unless otherwise specified; (e) descriptive headings are for convenience only and shall not control or affect the meaning of construction of part of the specification; and (f) "or" and "any" are not exclusive and "include" and "including" are not limiting. Further, the terms, "comprising," "having," "including," and "containing" are to be construed as open-ended terms (i.e., meaning "including but not limited to").

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether explicitly described.

To the extent necessary to provide descriptive support, the subject matter and/or text of the appended claims are incorporated herein by reference in their entirety.

Recitation of ranges of values herein are merely intended to serve as a shorthand method of referring individually to each separate value falling within the range of any subranges there between, unless otherwise clearly indicated herein. Each separate value within a recited range is incorporated into the specification or claims as if each separate value were individually recited herein. Where a specific range of values is provided, it is understood that each intervening value, to the tenth or less of the unit of the lower limit between the upper and lower limit of that range and any other stated or intervening value in that stated range of sub range thereof, is included herein unless the context clearly dictates otherwise. All subranges are also included. The upper and lower limits of these smaller ranges are also included therein, subject to any specifically and expressly excluded limit in the stated range.

It should be noted that some of the terms used herein are relative terms. For example, the terms, "upper" and, "lower" are relative to each other in location, i.e., an upper component is located at a higher elevation than a lower component in each orientation, but these terms can change if the orientation is flipped.

The terms, "horizontal" and "vertical" are used to indicate direction relative to an absolute reference, i.e., ground level. However, these terms should not be construed to require structure to be absolutely parallel or absolutely perpendicular to each other. For example, a first vertical structure and a second vertical structure are not necessarily parallel to each other. The terms, "top" and "bottom" or "base" are used to refer to locations or surfaces where the top is always higher than the bottom or base relative to an absolute reference, i.e., the surface of the Earth. The terms, "upwards" and "downwards" are also relative to an absolute reference; an upwards flow is always against the gravity of the Earth.

Orthopedic procedures frequently involve operating on a patient's joint. It will be understood that a joint typically comprises a multitude of orthopedic elements. It will further be appreciated that the exemplary methods and systems described herein can be applied to a variety of orthopedic elements. The examples described with reference to FIGS. 3, 5A and 5B relate to an exemplary knee joint for illustration purposes. It will be appreciated that the "orthopedic element" 100 referenced throughout this disclosure is not limited to the anatomy of a knee joint, but can include any skeletal structure and associated soft tissue, such as tendons, ligaments, cartilage, and muscle. A non-limiting list of example orthopedic elements 100 includes any partial or complete bone from a body, including but not limited to a femur, a tibia, a pelvis, a vertebra, a humerus, an ulna, a radius, a scapula, a skull, a fibula, a clavicle, a mandible, a rib, a carpal, a metacarpal, a tarsal, a metatarsal, a phalange, or any associated tendon, ligament, skin, cartilage, or muscle. It will be appreciated that an example operative area 170 can comprise several subject orthopedic elements 100.

Figure 3:
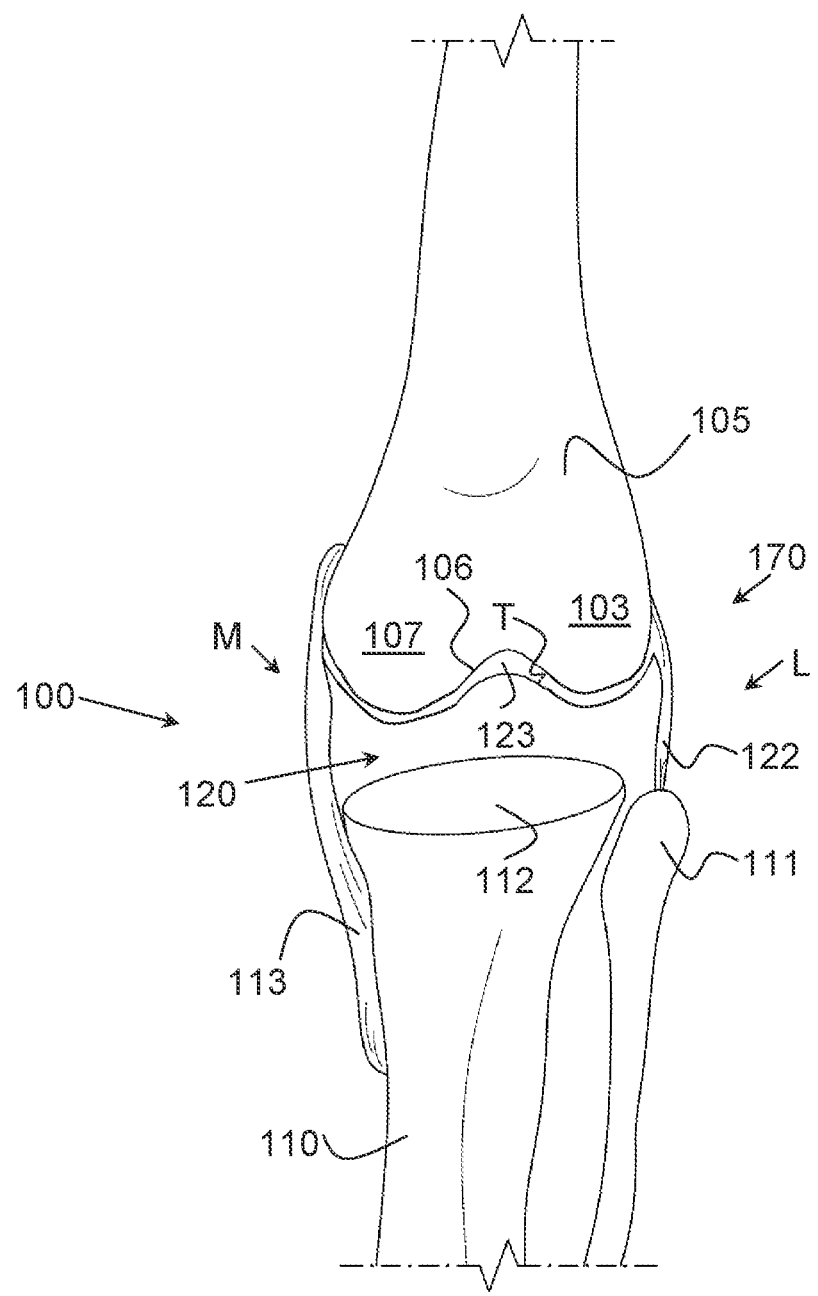
FIG. 3 is an anterior view of a simplified example left knee joint.

FIG. 3 is an anterior-posterior view of a simplified left knee joint 100 (i.e., an example joint operative area 170) in extension. The example knee joint 100 comprises a number of orthopedic elements, including a femur 105, a tibia 110, a fibula 111, a patella (not depicted), resected tibial plateau 112, femoral articular cartilage 123, a medial collateral ligament ("MCL") 113 engaging the distal femur 105 to the proximal tibia 110 on the medial side M, and a lateral collateral ligament ("LCL") 122 engaging the distal femur 105 to the fibula 111 on the lateral side L. The femoral articular cartilage 123 has a thickness T and the femoral articular cartilage 123 is engaged to the boney surface 106 of the distal femur 105. The distal femur further comprises a medial condyle 107 and the lateral condyle 103 (collectively, "femoral condyles"). The distal femur 105 is separated from the proximal tibia 110 by a femoral tibia gap 120. The perspective of FIG. 3 is an example of using a radiographic imaging technique to capture a first image of an orthopedic element (although in FIG. 3, multiple orthopedic elements, i.e., the femur 105, tibia 110, fibula 111, articular cartilage 123, MCL 113, and LCL 122 are depicted) in a first reference frame (see also FIG. 5A, which depicts the subject orthopedic element taken from a first reference frame, wherein the first reference frame captures the subject orthopedic element in the A-P position).

Figures 5A, 5B:
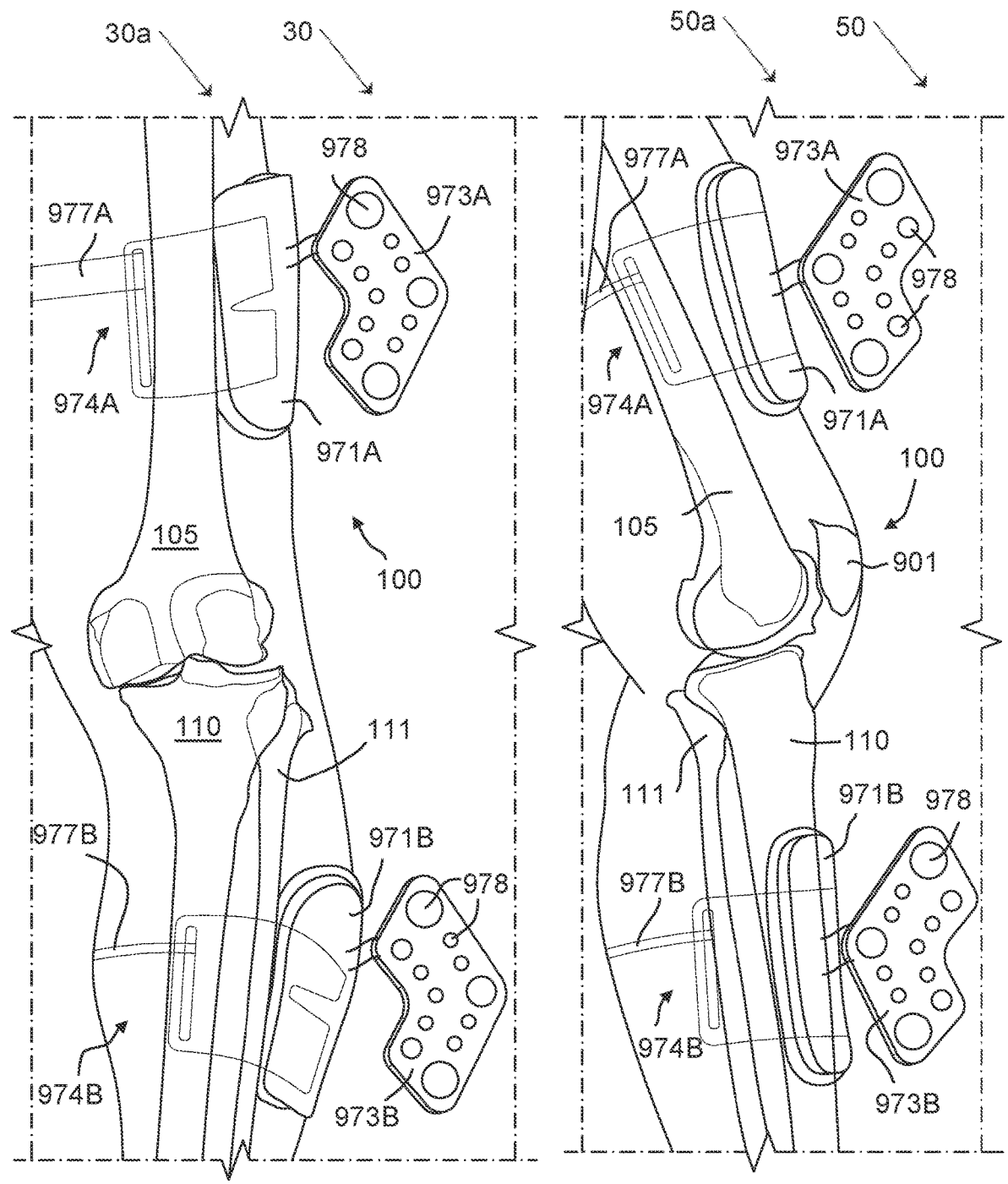
FIG. 5A is an image of subject orthopedic elements taken from the anterior-posterior ("A-P") position that shows an exemplary calibration jig.
FIG. 5B is an image of subject orthopedic elements of FIG. 5A taken from the medial-lateral ("M-L") position that shows an exemplary calibration jig.

FIG. 5B depicts the same subject orthopedic element in a second reference frame, wherein the second reference frame captures the subject orthopedic element in the M-L position.

In recent years, it has become possible to use 2D images, such as X-ray radiographs, to create 3D models of an operative area. These models can be used preoperatively to plan surgeries much closer to the date of the actual surgery. Moreover, these preoperative 3D models function as the native model from which surgical instruments themselves can be configured to fit exactly.

However, X-ray radiographs have typically not been used as inputs for 3D models previously because of concerns about image resolution and accuracy. X-ray radiographs are 2D representations of 3D space. As such, a 2D X-ray radiograph necessarily distorts the image subject relative to the actual object that exists in three dimensions. Furthermore, the object through which the X-ray passes can deflects the path of the X-ray as it travels from the X-ray source (typically the anode of the X-ray machine) to the X-ray detector (which may include by non-limiting example, X-ray image intensifiers, phosphorus materials, flat panel detectors "FPD" (including indirect conversion FPDs and direct conversion FPDs), or any number of digital or analog X-ray sensors or X-ray film). Defects in the X-ray machine itself or in its calibration can also undermine the usefulness of X-ray photogrammetry and 3D model reconstruction. Additionally, emitted X-ray photons have different energies. As the X-rays interact with the matter placed between the X-ray source and the detector, noise and artifacts can be produced in part because of Compton and Rayleigh scattering, the photoelectric effect, extrinsic variables in the environment or intrinsic variables in the X-ray generation unit, X-ray detector, and/or processing units or displays.

Moreover, in a single 2D image, the 3D data of the actual subject is lost. As such, there is no data that a computer can use from a single 2D image to reconstruct a 3D model of the actual 3D object. For this reason, CT scans, MRIs, and other imaging technologies that preserve third dimensional data were often preferred inputs for reconstructing models of one or more subject orthopedic elements (i.e., reconstructing a 3D model from actual 3D data generally resulted in more accurate, higher resolution models). However, certain exemplary embodiments of the present disclosure that are discussed below overcome these issues by using deep learning networks to improve the accuracy of reconstructed 3D models generated from X-ray input images.

By way of example, a deep learning algorithm, such as a convolutional neural network, can be used to generate a 3D model from a set of at least two 2D radiographic images of an operative area of a patient. In such a method, the deep learning algorithm can generate a model from the projective geometry data from the respective 2D images. The deep learning algorithm can have the advantage of being able to generate a mask of the different orthopedic elements (e.g., bones, soft tissue, etc.) in the operative area as well as being able to calculate a volume of the imaged or subject orthopedic element 100.

FIG. 1 is a flow chart outlining the steps of an exemplary method for generating patient-specific surgical guides (e.g., patient-specific drill guides or patient-specific resection guides). The method comprises: step 1a calibrating a radiographic imaging machine 1800 to determine a mapping relationship between radiographic image points and corresponding space coordinates to define spatial data 43, step 2a capturing a first image 30 of an orthopedic element 100 using a radiographic imaging technique, wherein the first image 30 defines a first reference frame 30a, step 3a capturing a second image 50 of the orthopedic element 100 using the radiographic imaging technique, wherein the second image 50 defines a second reference frame 50a, and wherein the first reference frame 30a is offset from the second reference frame 50a at an offset angle θ, step 4a projecting spatial data 43 from the first radiographic image 30 of the subject orthopedic element 100 and spatial data 43 from the second radiographic image 50 of the subject orthopedic element 100 to define volume data 75, step 5a using a deep learning network to detect the subject orthopedic element 100 using the spatial data 43, the spatial data 43 defining an anatomical landmark on or in the subject orthopedic element 100, step 6a using the deep learning network to apply a mask to the subject orthopedic element 100 defined by an anatomical landmark wherein spatial data 43 comprising image points disposed within a masked area of either the first image 30 or the second image 50 are given a first value and wherein spatial data 43 comprising image points disposed outside of the masked area of both the first image 30 and the second image 50 are given a second value, wherein the second value is different from the first value, step 7a calculating dimensions for a patient-specific surgical guide 500 configured to abut the orthopedic element.

Figure 2:
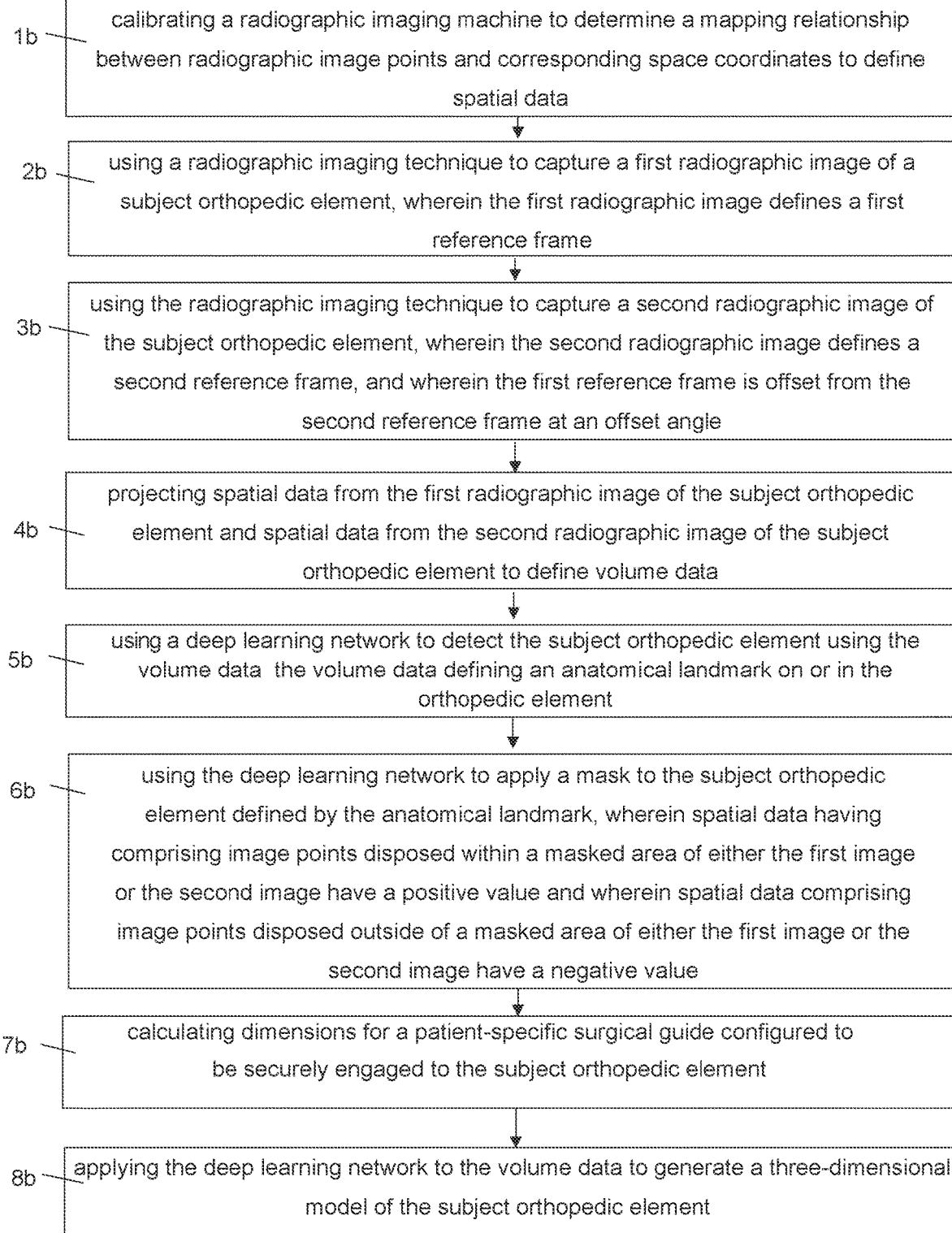
FIG. 2 is a flow chart illustrating steps of a further exemplary method.

In exemplary embodiments, an exemplary method may further comprise step 8b applying the deep learning network to the volume data 75 to generate a reconstructed 3D model of the orthopedic element. In other exemplary embodiments, step 5a or 5b can comprise detecting the spatial data 43 defining anatomical landmarks on or in the orthopedic element 100 using a deep learning network (see FIG. 2).

The above examples are provided for illustrative purposes and are in no way intended to limit the scope of this disclosure. All methods for generating a 3D model from 2D radiographic images of the same subject taken from at least two transverse positions are considered to be within the scope of this disclosure.

Figure 4:
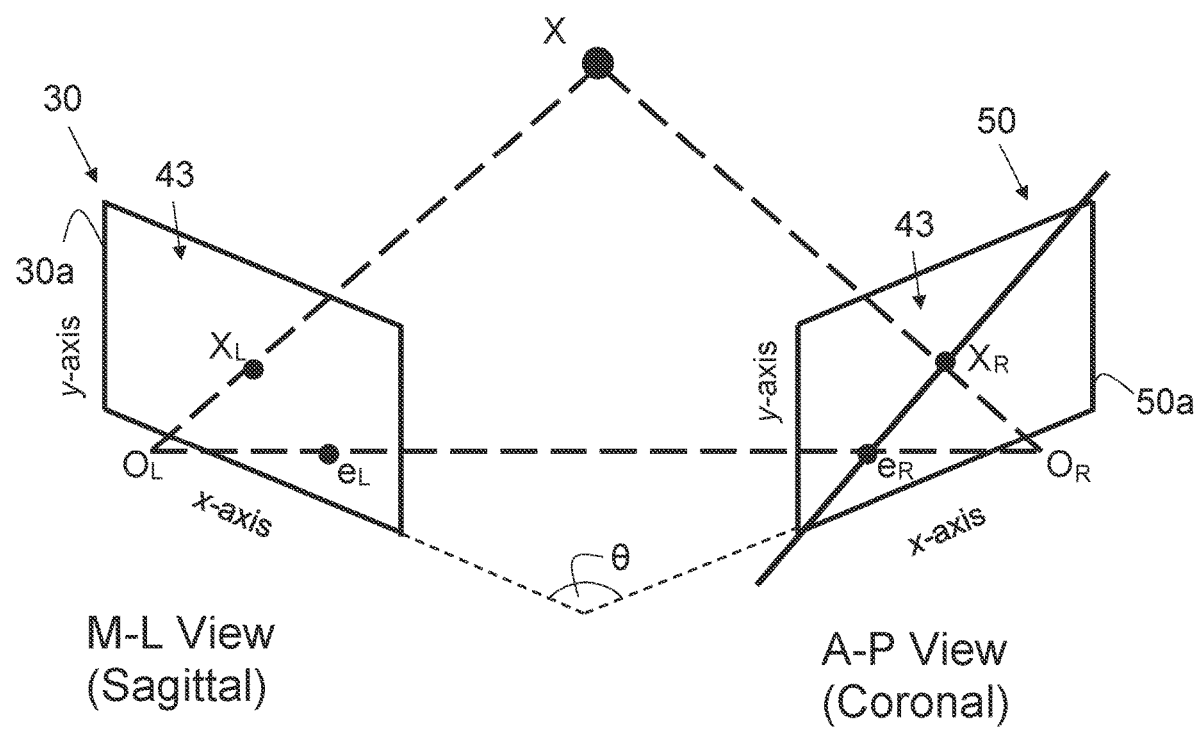
FIG. 4 is a schematic depiction of a pinhole camera model used to convey how principles of epipolar geometry can be used to ascertain the position of a point in 3D space from two 2D images taken from different reference frames from calibrated image detectors.
Figure 6:
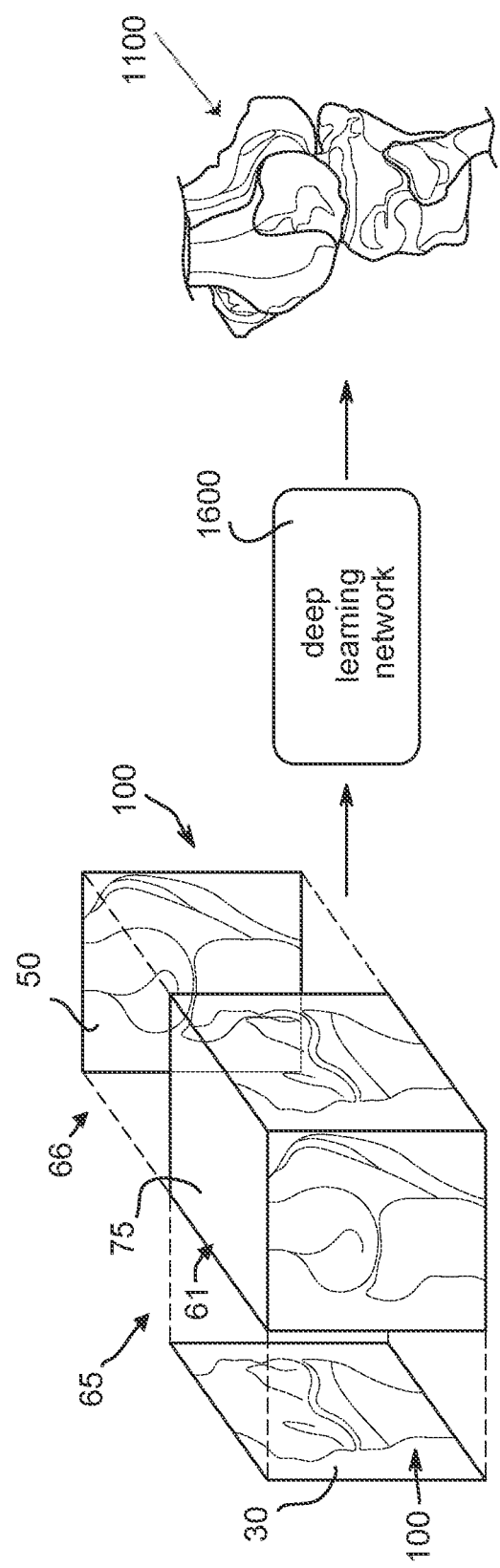
FIG. 6 is a schematic depiction of a system that uses a deep learning network to identify features (e.g., anatomical landmarks) of a subject orthopedic element to generate a 3D model of the subject orthopedic element.

FIGS. 4 and 6 illustrate how the first input image 30 and the second input image 50 can be combined to create a volume 61 comprising volume data 75 (FIG. 6). FIG. 4 illustrates basic principles of epipolar geometry than can be used to convert spatial data 43 from the respective input images 30, 50 into volume data 75. It will be appreciated that the spatial data 43 is defined by a collection of image points (e.g., $X_L$, $X_R$) mapped to corresponding space coordinates (e.g., x and y coordinates) for a given input image 30, 50.

Figure 9:
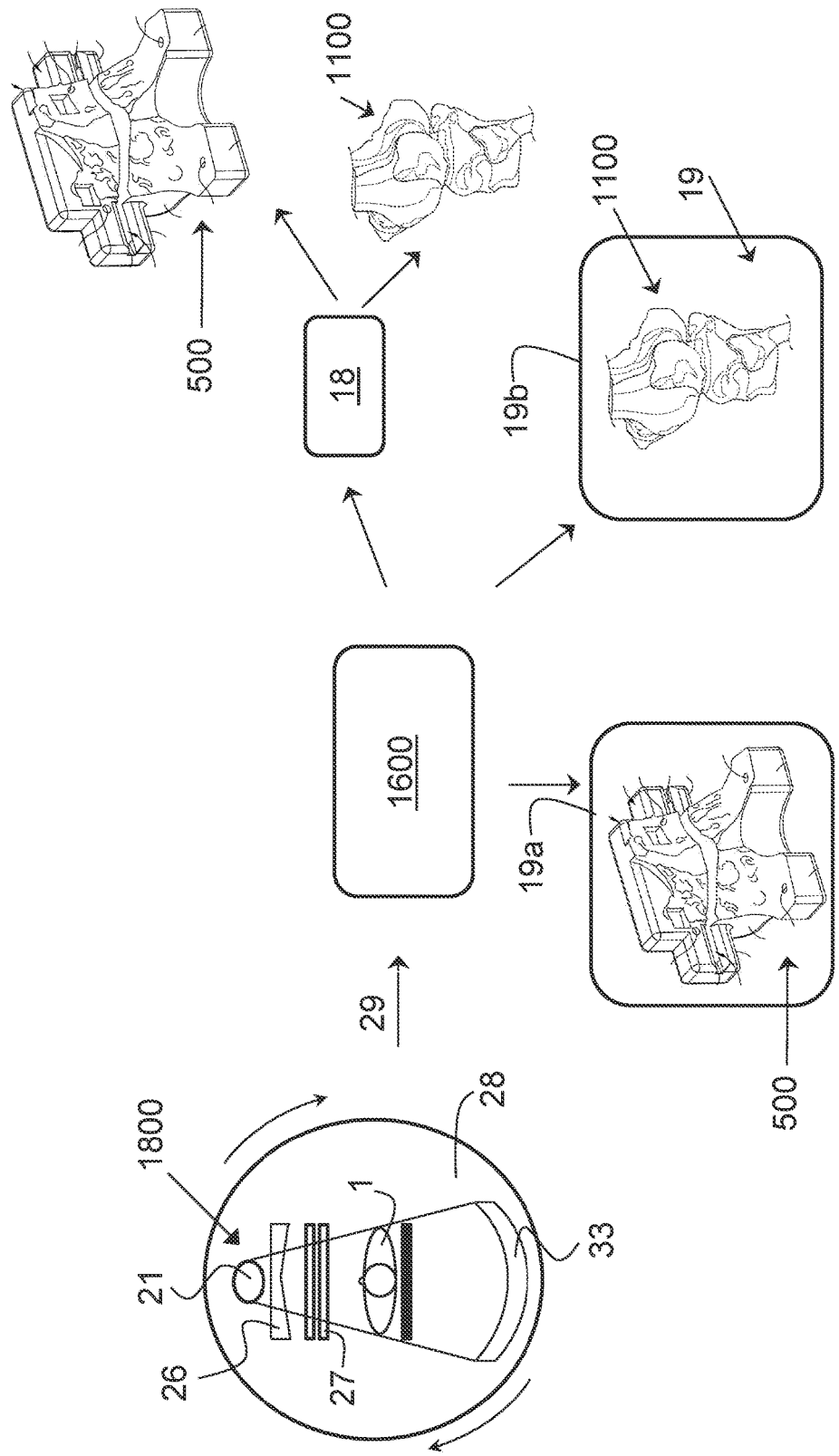
FIG. 9 is a schematic representation of an exemplary system.

FIG. 4 is a simplified schematic representation of a perspective projection described by the pinhole camera model. FIG. 4 conveys basic concepts related to computer stereo vison, but it is by no means the only method by which 3D models can be reconstructed from 2D stereo images. In this simplified model, rays emanate from the optical center (i.e., the point within a lens at which the rays of electromagnetic radiation (e.g., visible light, X-rays, etc.) from the subject object are assumed to cross within the imaging machine's sensor or detector array 33 (FIG. 9). The optical centers are represented by points $O_L$, $O_R$ in FIG. 4. In reality, the image plane (see 30a, 50a) is usually behind the optical center (e.g., $O_L$, $O_R$) and the actual optical center is projected onto the detector array 33 as a point, but virtual image planes (see 30a, 50a) are presented here for illustrating the principles more simply.

The first input image 30 is taken from a first reference frame 30a, while the second input image 50 is taken from a second reference frame 50a that is different from the first reference frame 30a. Each image comprise a matrix of pixel values. The first and second reference frames 30a, 50a are desirably offset from one another by an offset angle θ. The offset angle θ can represent the angle between the x-axis of the first reference frame 30a relative to the x-axis of the second reference frame 50a. Stated differently, the angle between the orientation of the orthopedic element in the first image and the orthopedic element in the second image can be known as the "offset angle."

Point $e_L$ is the location of the second input image's optical center $O_R$ on the first input image 30. Point $e_R$ is the location of the first input image's optical center $O_L$ on the second input image 50. Points $e_L$ and $e_R$ are known as "epipoles" or epipolar points and lie on line $O_L$-$O_R$. The points X, $O_L$, $O_R$ define an epipolar plane.

Because the actual optical center is the assumed point at which incoming rays of electromagnetic radiation from the subject object cross within the detector lens, in this model, the rays of electromagnetic radiation can actually be imagined to emanate from the optical centers $O_L$, $O_R$ for the purpose of visualizing how the position of a 3D point X in 3D space can be ascertained from two or more input images 30, 50 captured from a detector 33 of known relative position. If each point (e.g., $X_L$) of the first input image 30 corresponds to a line in 3D space, then if a corresponding point (e.g., $X_R$) can be found in the second input image, then these corresponding points (e.g., $X_L$, $X_R$) must be the projection of a common 3D point X. Therefore, the lines generated by the corresponding image points (e.g., $X_L$, $X_R$) must intersect at 3D point X. In general, if the value of X is calculated for every corresponding image points (e.g., $X_L$, $X_R$) in two or more input images 30, 50, a 3D volume 61 comprising volume data 75 can be reproduced from the two or more input images 30, 50. The value of any given 3D point X can be triangulated in a variety of ways. A non-limiting list of example calculation methods include the mid-point method, the direct linear transformation method, the essential matrix method, the line—line intersection method, and the bundle adjustment method.

It will be appreciated that "image points" (e.g., $X_L$, $X_R$) described herein may refer to a point in space, a pixel, a portion of a pixel, or a collection of adjacent pixels. It will also be appreciated that 3D point X as used herein can represent a point in 3D space. In certain exemplary applications, 3D point X may be expressed as a voxel, a portion of a voxel, or a collection of adjacent voxels.

However, before principles of epipolar geometry can be applied, the position of each image detector 33 relative to the other image detector(s) 33 must be determined (or the position of a sole image detector 33 must be determined at the point in time in which the first image 30 was taken and the adjusted position of the sole image detector 33 should be known at the point in time in which the second image 50 was taken). It is also desirable to determine the focal length and the optical center of the imaging machine 1800. To ascertain this practically, the image detector 33 (or image detectors) is/are first calibrated. FIGS. 5A and 5B depict calibration jigs 973A, 973B relative to subject orthopedic elements 100. In these figures, the example orthopedic elements 100 are the distal aspect of the femur 105 and the proximal aspect of the tibia 110 that comprise a knee joint. The proximal fibula 111 is another orthopedic element 100 imaged in FIGS. 5A and 5B. The patella 901 is another orthopedic element 100 shown in FIG. 5B.

FIG. 5A is an anterior-posterior view of the example orthopedic elements 100 (i.e., FIG. 5A represents a first image 30 taken from a first reference frame 30a (e.g., a first transverse position)). A first calibration jig 973A is attached to a first holding assembly 974A. The first holding assembly 974A may comprise a first padded support 971A engaged to a first strap 977A. The first padded support 971A is attached externally to the patient's thigh via the first strap 977A. The first holding assembly 974A supports the first calibration jig 973A oriented desirably parallel to the first reference frame 30a (i.e., orthogonal to the detector 33). Likewise, a second calibration jig 973B that is attached to a second holding assembly 974B may be provided. The second holding assembly 974B may comprise a second padded support 971B engaged to a second strap 977B. The second padded support 971B is attached externally to the patient's calf via the second strap 977B. The second holding assembly 974B supports the second calibration jig 973B desirably parallel to the first reference frame 30a (i.e., orthogonal to the detector 33). The calibration jigs 973A, 973B are desirably positioned sufficiently far away from the subject orthopedic elements 100 such that the calibration jigs 973A, 973B do not overlap any subject orthopedic element 100.

FIG. 5B is a medial-lateral view of the example orthopedic elements 100 (i.e., FIG. 5B represents a second image 50 taken from a second reference frame 50a (e.g., a second transverse position)). In the depicted example, the medial-lateral reference frame 50a is rotated or "offset" 90° from the anterior-posterior first reference frame 30a. The first calibration jig 973A is attached to the first holding assembly 974A. The first holding assembly 974A may comprise a first padded support 971A engaged to a first strap 977A. The first padded support 971A is attached externally to the patient's thigh via the first strap 977A. The first holding assembly 974A supports the first calibration jig 973A desirably parallel to the second reference frame 50a (i.e., orthogonal to the detector 33). Likewise, a second calibration jig 973B that is attached to a second holding assembly 974B may be provided. The second holding assembly 974B may comprise a second padded support 971B engaged to a second strap 977B. The second padded support 971B is attached externally to the patient's calf via the second strap 977B. The second holding assembly 974B supports the second calibration jig 973B desirably parallel to the second reference frame 50a (i.e., orthogonal to the detector 33). The calibration jigs 973A, 973B are desirably positioned sufficiently far away from the subject orthopedic elements 100 such that the calibration jigs 973A, 973B do not overlap any subject orthopedic element 100.

The patient can desirably be posited in the standing position (i.e., the leg is in extension) because the knee joint is stable in this orientation (see FIG. 9). Preferably, the patient's distance relative to the imaging machine should not be altered during the acquisition of the input images 30, 50. The first and second images 30, 50 need not capture the entire leg, rather the image can focus on the joint that will be the subject of the operative area 170.

It will be appreciated that depending upon the subject orthopedic element 100 to be imaged and modeled, only a single calibration jig 973 may be used. Likewise, if a particularly long collection of orthopedic elements 100 are to be imaged and modeled, more than two calibration jigs may be used.

Each calibration jig 973A, 973B is desirably of a known size. Each calibration jig 973A, 973B desirably has at least four or more calibration points 978 distributed throughout. The calibration points 978 are distributed in a known pattern in which the distance from one point 978 relative to the others is known. The distance from the calibration jig 973 from an orthopedic element 100 can also be desirably known. For calibration of an X-ray photogrammetry system, the calibration points 978 may desirably be defined by metal structures on the calibration jig 973. Metal typically absorbs most X-ray beams that contact the metal. As such, metal typically appears very brightly relative to material that absorbs less of the X-rays (such as air cavities or adipose tissue). Common example structures that define calibration points include reseau crosses, circles, triangles, pyramids, and spheres.

These calibration points 978 can exist on a 2D surface of the calibration jig 973, or 3D calibration points 978 can be captured as 2D projections from a given image reference frame. In either situation, the 3D coordinate (commonly designated the z coordinate) can be set to equal zero for all calibration points 978 captured in the image. The distance between each calibration point 978 is known. These known distances can be expressed as x, y coordinates on the image sensor/detector 33. To map a point in 3D space to a 2D coordinate pixel on a sensor 33, the dot product of the detector's calibration matrix, the extrinsic matrix and the homologous coordinate vector of the real 3D point can be used. This permits the real world coordinates of a point in 3D space to be mapped relative to calibration jig 973. Stated differently, this generally permits the x, y coordinates of the real point in 3D space to be transformed accurately to the 2D coordinate plane of the image detector's sensor 33 to define spatial data 43 (see FIG. 4).

The above calibration method is provided as an example. It will be appreciated that all methods suitable for calibrating an X-ray photogrammetry system are considered to be within the scope of this disclosure. A non-limiting list of other X-ray photogrammetry system calibration methods include the use of a reseau plate, the Zhang method, the bundle adjustment method, direct linear transformation methods, maximum likelihood estimation, a k-nearest neighbor regression approach ("kNN"), other deep learning methods, or combinations thereof.

FIG. 6 illustrates how the calibrated input images 30, 50, when oriented along the known offset angle θ, can be back projected into a 3D volume 61 comprising two channels 65, 66. The first channel 65 contains all the image points (e.g., $X_L$ etc.) of the first input image 30 and the second channel 66 contains all the image points (e.g., $X_R$ etc.) of the second input image 50. That is, each image point (e.g., pixel) is replicated over its associated back-projected 3D ray. Next, epipolar geometry can be used to generate a volume 61 of the imaged operative area 170 comprising volume data 75 from these back projected 2D input images 30, 50.

Referring to FIG. 6, the first image 30 and the second image 50 desirably have known image dimensions. The dimensions may be pixels. For example, the first image 30 may have dimensions of 128×128 pixels. The second image 50 may have dimensions of 128×128 pixels. The dimensions of the input images 30, 50 used in a particular computation desirably have consistent dimensions. Consistent dimensions may be desirable for later defining a cubic working area of regular volume 61 (e.g., a 128×128×128 cube). As seen in FIG. 4, the offset angle θ is desirably 90°. However, other offset angles θ may be used in other exemplary embodiments.

In the depicted example, each of the 128×128 pixel input images 30, 50 are replicated 128 times over the length of the adjacent input image to create a volume 61 having dimensions of 128×128×128 pixels. That is, the first image 30 is copied and stacked behind itself at one copy per pixel for 128 pixels while the second image 50 is copied and stacked behind itself for 128 pixels such that stacked images overlap to thereby create the volume 61. In this manner, the volume 61 can be said to comprise two channels 65, 66, wherein the first channel 65 comprises the first image 30 replicated n times over the length of the second image 50 (i.e., the x-axis of the second image 50) and the second channel 66 comprises the second image 50 replicated m times over the length of the first image 30 (i.e., the x-axis of the first image 30), wherein "n" and "m" are the length of the indicated image as expressed as the number of pixels (or other dimensions on other exemplary embodiments) that comprise the length of the indicated image. If the offset angle θ is known, each transverse slice (also known as an "axial slice" by some radiologists) of the volume 61 creates an epipolar plane comprising voxels that are back-projected from the pixels that comprise the two epipolar lines. In this manner, projecting spatial data 43 from the first image 30 of the subject orthopedic element 100 and the spatial data 43 from the second image 50 of the subject orthopedic element 100 defines the volume data 75. Using this volume data 75, the 3D representation can be reconstructed using epipolar geometric principles as discussed above; the 3D representation is consistent geometrically with the information in the input images 30, 50.

In exemplary systems and methods for generating patient-specific surgical guides 500 using a deep learning network, wherein the deep learning network is a CNN, a detailed example of how the CNN can be structured and trained is provided. All architecture of CNNs are considered to be within the scope of this disclosure. Common CNN architectures include by way of example, LeNet, GoogLeNet, AlexNet, ZFNet, ResNet, and VGGNet.

Figure 11:
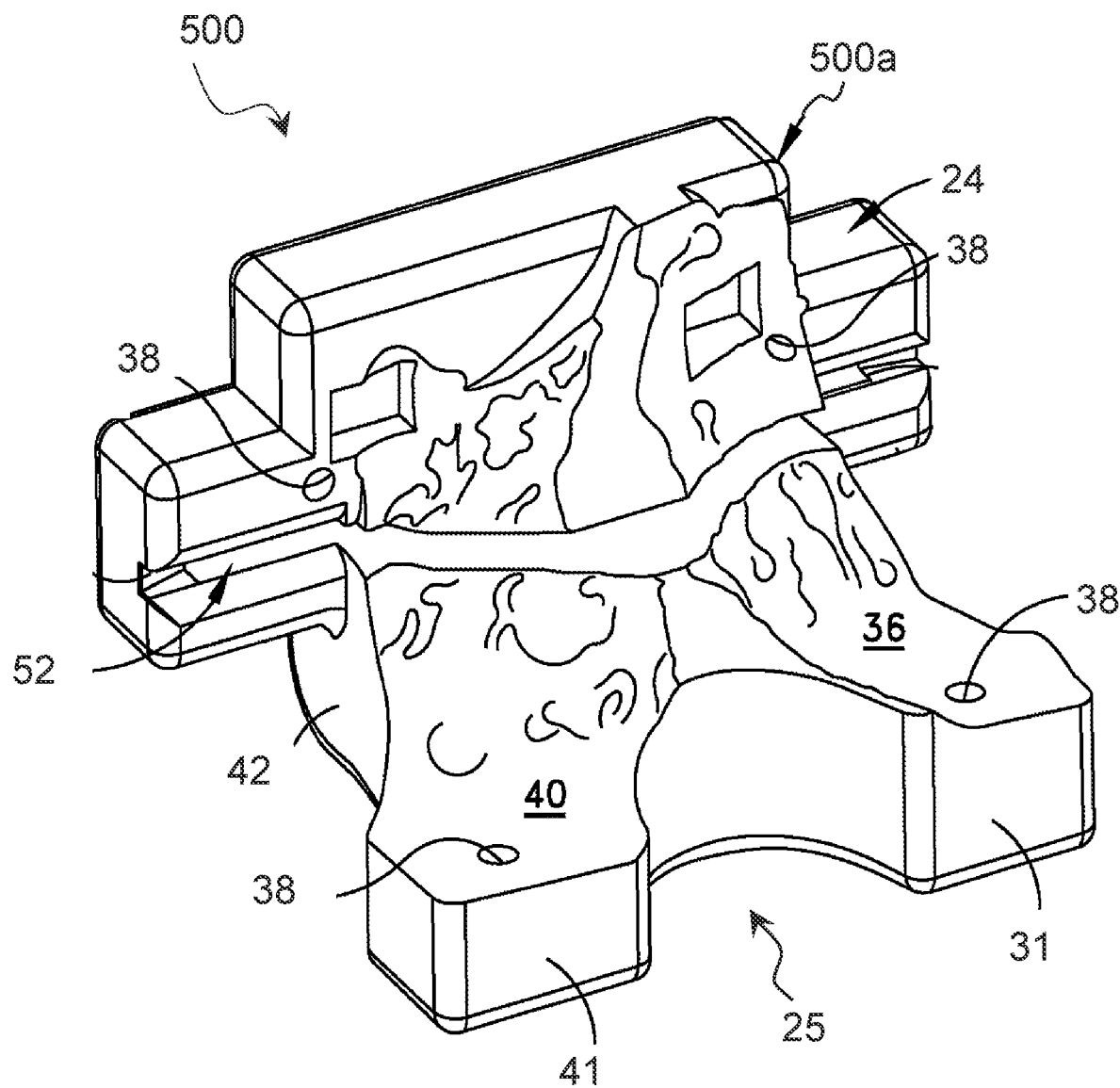
FIG. 11 is the view of the underside of an exemplary patient-specific surgical guide created according to any exemplary method disclosed herein.
Figure 13:
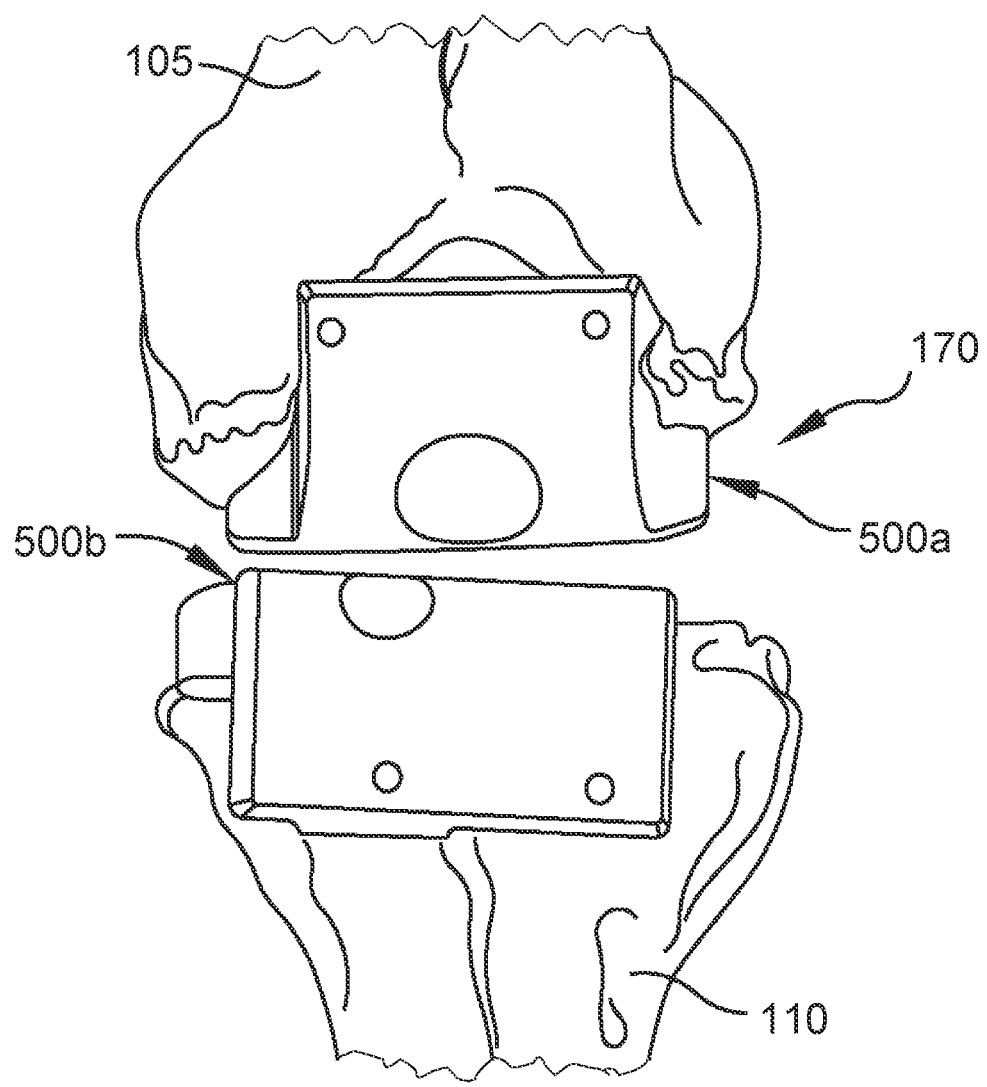
FIG. 13 depicts an exemplary patient-specific femoral resection guide mount securely engaged to the patient's distal femur and an exemplary patient-specific tibial resection guide mount securely fixed to the patient's proximal tibia.

FIG. 11 is the view of the underside of a patient-specific surgical guide 500 created according to any exemplary method disclosed herein. In FIG. 13, the patient-specific surgical guide 500 is securely engaged to the orthopedic element 100 (which is a femur 105 in the depicted example). The patient-specific surgical guide 500 can be formed from a resilient polymer material. The patient-specific surgical guide 500 depicted in FIG. 11 is a patient-specific femoral resection guide mount 500a configured to securely engage the condyles 107, 103 of the patient's specific operative femur 105. The depicted exemplary patient-specific femoral resection guide mount 500a comprises a body 42 having a resection slot 52 extending transversely through the body 42 and a bifurcated condylar yoke 25 and a guide receptacle 24. The bifurcated condylar yoke 25 comprises a pair of spaced apart arms 31, 41 that project outwardly from the body 42. The first arm 31 has a first mating surface 36 that is complementary to the anatomical surface features of a selected region of the patient's natural bone (e.g., one of the patient's distal femoral condyles). Likewise, the second arm 41 has a second mating surface 40 that is complementary to the anatomical surface features of a selected region of the patient's natural bone (e.g., the other of the patient's distal femoral condyles). A through bore 38 may optionally extend through each spaced apart arm 31, 41. A pin may optionally be inserted through each of the through bores 38 to further secure the depicted patient-specific surgical guide 500 to the patient's natural bone.

In exemplary embodiments, the curved body 42 of the patient-specific surgical guide 500 may store potential energy when the patient-specific surgical guide 500 abuts the surface topography of the patient's natural exposed bone (see 106, FIG. 3). In this manner, the curved body 42 and the complementary mating surfaces 36, 40 that match the surface topography of the patient's natural exposed bone can allow the patient-specific surgical guide 500 to be "press-fit" (i.e., be secured by friction) to the patient's exposed femoral condyles at the desired location.

Once the patient-specific surgical guide 500 abuts and is securely engaged to the complementary portions of the patient's exposed bone in the desired location, the surgeon can insert a surgical saw through the resection slot 52 to resect the patient's distal femur 105 at the desired location in preparation for implant sizing and fitting. It is contemplated that making custom surgical guides 500 in a manner consistent with this disclosure may permit placement of a surgical saw more accurately and precisely and closer in time and using less energy than was previously possible.

Figure 12:
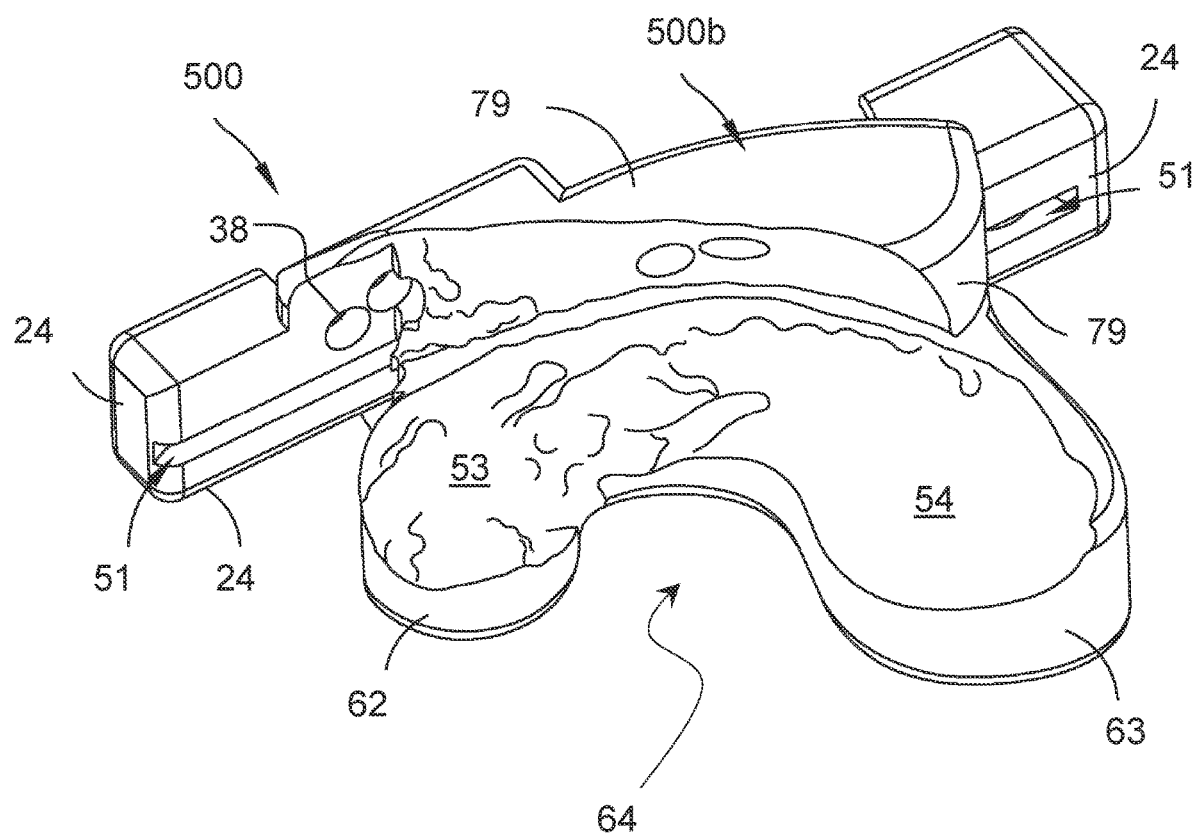
FIG. 12 is the view of the underside of another exemplary patient-specific surgical guide created according to any exemplary method disclosed herein.

FIG. 12 is the view of the underside of another exemplary patient-specific surgical guide 500 created according to any exemplary method disclosed herein. In FIG. 12, the patient-specific surgical guide 500 is a tibial resection guide mount 500b.

The depicted exemplary patient-specific tibial resection guide mount 500b comprises a body 79 having a resection slot 51 extending transversely through the body 79 and a bifurcated condylar yoke 64 and a guide receptacle 24. The bifurcated condylar yoke 64 comprises a pair of spaced apart arms 62, 63 that project outwardly from the body 79. The first arm 62 has a first mating surface 53 that is complementary to the anatomical surface features of a selected region of the patient's natural bone (e.g., one of the patient's proximal tibial hemi-plateau condyles). Likewise, the second arm 63 has a second mating surface 54 that is complementary to the anatomical surface features of a selected region of the patient's natural bone (e.g., the other of the patient's proximal tibial hemi-plateau). A through bore 38 may optionally extend through the body 79. A pin may optionally be inserted through each of the through bores 38 to further secure the depicted patient-specific tibial resection guide mount 500b to the patient's natural bone.

In embodiments, the first and second mating surfaces 53, 54 of the patient-specific tibial resection guide mount 500b can permit the patient-specific tibial resection guide mount 500b to be secured to the precise location of the patient's proximal tibial via friction. Once properly seated and secured, a surgeon may insert a surgical saw through the tibial resection slot 51 to resect the plateau of the proximal tibia.

FIG. 13 depicts patient-specific femoral resection guide mount 500a securely engaged to the patient's distal femur 105 and the patient-specific tibial resection guide mount 500b securely fixed to the patient's proximal tibia 110.

Because the patient-specific surgical guide 500 was designed and manufactured using technical specifications derived from 3D spatial data, which was in turn derived from two radiographic images of the orthopedic element 100 taken from different reference frames, the patient-specific surgical guide 500 precisely fits the orthopedic element 100 per the preoperative plan. Moreover, because radiography is generally more efficient and easier to obtain than CT or MRI scans, it is contemplated that preoperative planning can occur closer to the date of the scheduled surgical procedure and thereby mitigate the potential for change between the pre-operative planning and the actual anatomy on the day of the surgery.

It is further contemplated that preoperative planning can even occur on the same day as the scheduled surgery, especially if additive manufacturing machines (e.g., 3D printing machines) or subtractive manufacturing machines (e.g., CNC machines) are present onsite or locally. For example, a patient may undergo preoperative imagine and planning in the morning and have surgery schedule for the afternoon.

Figure 7:
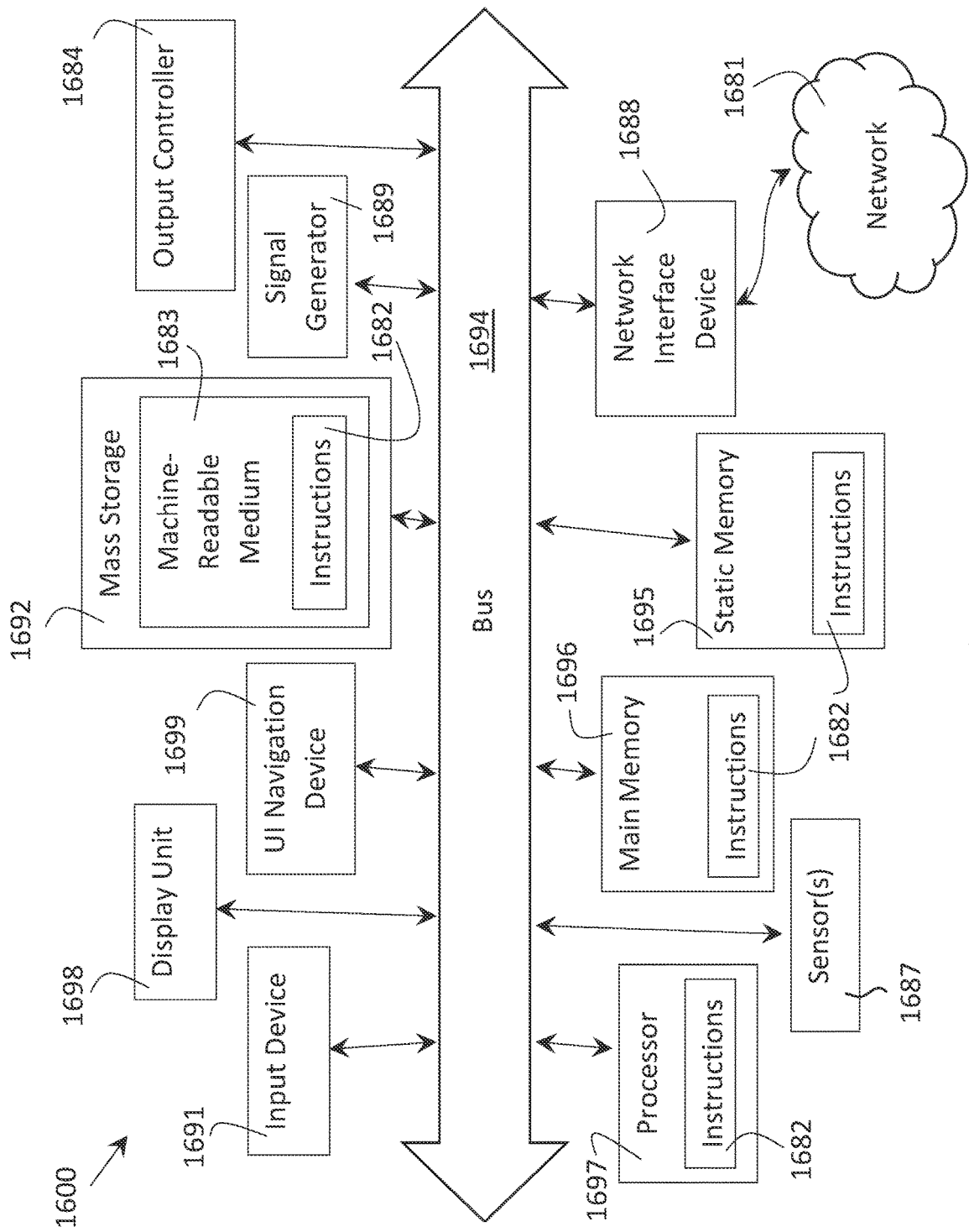
FIG. 7 is a schematic representation of a system configured to generate a model of an orthopedic element and to calculate dimensions for a patient-specific surgical guide configured to abut the orthopedic element from using two or more tissue penetrating, flattened, input images taken of the same subject orthopedic element from calibrated detectors at an offset angle.

Preferably, the methods disclosed herein may be implemented on a computer platform having hardware such as one or more central processing units (CPU), a random access memory (RAM), and input/output (I/O) interface(s) (see FIG. 7).

In still other embodiments, a volume of the orthopedic element may be calculated. It will be appreciated that any disclosed calculations or the results of any such calculations may optionally be displayed on a display.

It is further contemplated that the exemplary methods disclosed herein may be used for preoperative planning, intraoperative planning or execution, or postoperative evaluation of the implant placement and function.

Referring to FIG. 9, an exemplary system for calculating the dimensions of a patient-specific surgical guide 500 configured to abut or be securely engaged to the subject orthopedic element 100 can comprise: a radiographic imaging machine 1800 comprising an emitter 21 and a detector 33 (FIG. 9), wherein the detector 33 of the radiographic imaging machine 1800 captures a first image 30 (FIGS. 4 and 5A) in a first transversion position 30a (FIGS. 4 and 5A) and a second image 50 (FIGS. 4 and 5B) in a second transverse position 50a (FIGS. 4 and 5B), wherein the first transverse position 30a is offset from the second transverse position 50a by an offset angle θ (FIG. 4), a transmitter 29 (FIG. 9), and a computational machine 1600 (see FIG. 7 for further details) wherein the transmitter 29 transmits the first image 30 and the second image 50 from the detector 33 to the computational machine 1600, and wherein the computational machine 1600 is configured to calculate a surface topography of the subject orthopedic element 100. In certain exemplary embodiments, the computational machine 1600 can be configured to calculate dimensions of a mating surface of the patient specific surgical guide 500 that are complementary to the surface topography of a portion of the subject orthopedic element 100.

In certain exemplary embodiments, an exemplary system may further comprise a display 19.

In certain exemplary embodiments, an exemplary system may further comprise a manufacturing machine 18. In exemplary embodiment comprising a manufacturing machine 18, the manufacturing machine 18 can be an additive manufacturing machine. In such embodiments, the additive manufacturing machine may be used to manufacture the 3D model of the subject orthopedic element 1100 or a physical 3D model of the patient-specific surgical guide 500. By way of example, 3D manufacturing techniques can include, but are not limited to stereo lithography and laser sintering.

FIG. 9 is a schematic representation of an exemplary system comprising a radiographic imaging machine 1800 comprising an X-ray source 21, such as an X-ray tube, a filter 26, a collimator 27, and a detector 33. In FIG. 9, the radiographic imaging machine 1800 is shown from the top down. A patient 1 is disposed between the X-ray source 21 and the detector 33. The radiographic imaging machine 1800 may be mounted on a rotatable gantry 28. The radiographic imaging machine 1800 may take a radiographic image of the patient 1 from a first reference frame 30a. The gantry 28 may then rotate the radiographic imaging machine 1800 by an offset angle (preferably 90°). The radiographic imaging machine 1800 may then take the second radiographic image 50 from the second reference frame 50a. It will be appreciated that other exemplary embodiments can comprise using multiple input images taken at multiple offset angles θ. In such embodiments, the offset angle may be less than or greater than 90° between adjacent input images.

It will be appreciated that the offset angle need not be exactly 90 degrees in every embodiment. An offset angle having a value within a range that is plus or minus 45 degrees is contemplated as being sufficient. In other exemplary embodiments, an operator may take more than two images of the orthopedic element using a radiographic imaging technique. It is contemplated that each subsequent image after the second image can define a subsequent image reference frame. For example, a third image can define a third reference frame, a fourth image can define a fourth reference frame, the $n^{th}$ image can define an $n^{th}$ reference frame, etc.

In exemplary embodiments comprising three input images and three distinct reference frames, each of the three input images desirably have an offset angle θ of about 60 degrees relative to each other. In exemplary embodiments comprising four input images and four distinct reference frames, the offset angle θ is desirably 45 degrees from an adjacent reference frame. In an exemplary embodiment comprising five input images and five distinct reference frames, the offset angle θ is desirably about 36 degrees from the adjacent reference frame. In exemplary embodiments comprising n images and n distinct reference frames, the offset angle θ is desirably 180/n degrees.

It is further contemplated that embodiments involving multiple images, especially more than two images do not necessarily have to have regular and consistent offset angles. For example, an exemplary embodiment involving four images and four distinct reference frames may have a first offset angle at 85 degrees, a second offset angle at 75 degrees, a third offset angle at 93 degrees, and a fourth offset angle at 107 degrees.

A transmitter 29 then transmits the first image 30 and the second image 50 to a computational machine 1600. The computational machine 1600 can apply a deep learning network to calculate dimensions of a mating surface of the patient-specific surgical guide 500 that are complementary to the surface topography of a portion of the subject orthopedic element 100 in any manner that is consistent with this disclosure. FIG. 9 further depicts the output of the computational machine 1600 being transmitted to a manufacturing machine 18. The manufacturing machine 18 can be an additive manufacturing machine, such as a 3D printer, (e.g., stereo lithography or laser sintering manufacturing equipment), or the manufacturing machine can be a subtractive manufacturing machine, such as a computer numerical control ("CNC") machine. In yet other exemplary embodiments, the manufacturing machine 18 can be a casting mold. The manufacturing machine 18 can use the output data from the computational machine 1600 to produce a physical model of one or more 3D models of the subject orthopedic elements 1100. In this manner, the manufacturing machine 18 can be said to be "configured to produce" at least a partial physical model of the identified surface of the orthopedic element 100. In embodiments, the manufacturing machine can be used to produce a physical 3D model of the patient-specific surgical guide 500.

FIG. 9 also depicts another embodiment in which the output data from the computational machine 1600 is transmitted to a display 19. A first display 19a depicts a virtual 3D model of the patient-specific surgical guide 500. The second display 19b depicts a virtual 3D model of the identified subject orthopedic element 1100.

This display 19 may take the form of a screen. In other exemplary embodiments, the display 19 may comprise a glass or plastic surface that is worn or held by the surgeon or other people in the operation theater. Such a display 19 may comprise part of an augmented reality device, such that the display shows the 3D model in addition to the bearer's visual field. In certain embodiments, such a 3D model can be superimposed on the actual operative joint. In yet other exemplary embodiments, the 3D model can be "locked" to one or more features of the operative orthopedic element 100, thereby maintaining a virtual position of the 3D model relative to the one or more features of the operative orthopedic element 100 independent of movement of the display 19. It is still further contemplated that the display 19 may comprise part of a virtual reality system in which the entirety of the visual field is simulated.

Although X-ray radiographs from an X-ray imaging system may be desirable because X-ray radiographs are relatively inexpensive compared to CT scans and because the equipment for some X-ray imaging systems, such as a fluoroscopy system, are generally sufficiently compact to be used intraoperatively, nothing in this disclosure limits the use of the 2D images to X-ray radiographs unless otherwise expressly claimed, nor does anything in this disclosure limit the type of imaging system to an X-ray imaging system. Other 2D images can include by way of example: CT-images, CT-fluoroscopy images, fluoroscopy images, ultrasound images, positron emission tomography ("PET") images, and MRI images. Other imaging systems can include by way of example: CT, CT-fluoroscopy, fluoroscopy, ultrasound, PET, and MRI systems.

Preferably, the exemplary methods can be implemented on a computer platform (e.g., a computational machine 1600) having hardware such as one or more central processing units (CPU), a random access memory (RAM), and input/output (I/O) interface(s). An example of the architecture for an example computational machine 1600 is provided below with reference to FIG. 7.

FIG. 7 generally depicts a block diagram of an exemplary computational machine 1600 upon which one or more of the methods discussed herein may be performed in accordance with some exemplary embodiments. In certain exemplary embodiments, the computational machine 1600 can operate on a single machine. In other exemplary embodiments, the computational machine 1600 can comprise connected (e.g., networked) machines. Examples of networked machines that can comprise the exemplary computational machine 1600 include by way of example, cloud computing configurations, distributed hosting configurations, and other computer cluster configurations. In a networked configuration, one or more machines of the computational machine 1600 can operate in the capacity of a client machine, a server machine, or both a server-client machine. In exemplary embodiments, the computational machine 1600 can reside on a personal computer ("PC"), a mobile telephone, a tablet PC, a web appliance, a personal digital assistant ("PDA"), a network router, a bridge, a switch, or any machine capable of executing instructions that specify actions to be undertaken by said machine or a second machine controlled by said machine.

Example machines that can comprise the exemplary computational machines 1600 can include by way of example, components, modules, or like mechanisms capable of executing logic functions. Such machines may comprise tangible entities (e.g., hardware) that is capable of carrying out specified operations while operating. As an example, the hardware may be hardwired (e.g., specifically configured) to execute a specific operation. By way of example, such hardware may have configurable execution media (e.g., circuits, transistors, logic gates, etc.) and a computer-readable medium having instructions, wherein the instructions configure the execution media to carry out a specific operation when operating. The configuring can occur via a loading mechanism or under the direction of the execution media. The execution media selectively communicate to the computer-readable medium when the machine is operating. By way of an example, when the machine is in operation, the execution media may be configured by a first set of instructions to execute a first action or set of actions at a first point in time and then reconfigured at a second point in time by a second set of instructions to execute a second action or set of actions.

The exemplary computational machine 1600 may include a hardware processor 1697 (e.g., a CPU, a graphics processing unit ("GPU"), a hardware processor core, or any combination thereof, a main memory 1696 and a static memory 1695, some or all of which may communicate with each other via an interlink (e.g., a bus) 1694. The computational machine 1600 may further include a display unit 1698, an input device 1691 (preferably an alphanumeric or character-numeric input device such as a keyboard), and a user interface ("UP") navigation device 1699 (e.g., a mouse or stylus). In an exemplary embodiment, the input device 1691, display unit 1698, and UI navigation device 1699 may be a touch screen display. In exemplary embodiments, the display unit 1698 may include holographic lenses, glasses, goggles, other eyewear, or other AR or VR display components. For example, the display unit 1698 may be worn on a head of a user and may provide a heads-up-display to the user. The input device 1691 may include a virtual keyboard (e.g., a keyboard displayed virtually in a virtual reality ("VR") or an augmented reality ("AR") setting) or other virtual input interface.

The computational machine 1600 may further include a storage device (e.g., a drive unit) 1692, a signal generator 1689 (e.g., a speaker) a network interface device 1688, and one or more sensors 1687, such as a global positioning system ("GPS") sensor, accelerometer, compass, or other sensor. The computational machine 1600 may include an output controller 1684, such as a serial (e.g., universal serial bus ("USB"), parallel, or other wired or wireless (e.g., infrared ("IR") near field communication ("NFC"), radio, etc.) connection to communicate or control one or more ancillary devices.

The storage device 1692 may include a machine-readable medium 1683 that is non-transitory, on which is stored one or more sets of data structures or instructions 1682 (e.g., software) embodying or utilized by any one or more of the functions or methods described herein. The instructions 1682 may reside completely or at least partially, within the main memory 1696, within static memory 1695, or within the hardware processor 1697 during execution thereof by the computational machine 1600. By way of example, one or any combination of the hardware processor 1697, the main memory 1696, the static memory 1695, or the storage device 1692, may constitute machine-readable media.

While the machine-readable medium 1683 is illustrated as a single medium, the term, "machine readable medium" may include a single medium or multiple media (e.g., a distributed or centralized database, or associated caches and servers) configured to store the one or more instructions 1682.

The term "machine-readable medium" may include any medium that is capable of storing, encoding, or carrying instructions for execution by the computational machine 1600 and that cause the computational machine 1600 to perform any one or more of the methods of the present disclosure, or that is capable of storing, encoding, or carrying data structures used by or associated with such instructions. A non-limited example list of machine-readable media may include magnetic media, optical media, solid state memories, non-volatile memory, such as semiconductor memory devices (e.g., electronically erasable programmable read-only memory ("EEPROM"), electronically programmable read-only memory ("EPROM"), and magnetic discs, such as internal hard discs and removable discs, flash storage devices, magneto-optical discs, and CD-ROM and DVD-ROM discs.

The instructions 1682 may further be transmitted or received over a communications network 1681 using a transmission medium via the network interface device 1688 utilizing any one of a number of transfer protocols (e.g., internet protocol ("IP"), user datagram protocol ("UDP"), frame relay, transmission control protocol ("TCP"), hypertext transfer protocol ("HTTP"), etc.) Example communication networks may include a wide area network ("WAN"), a plain old telephone ("POTS") network, a local area network ("LAN"), a packet data network, a mobile telephone network, a wireless data network, and a peer-to-peer ("P2P") network. By way of example, the network interface device 1688 may include one or more physical jacks (e.g., Ethernet, coaxial, or phone jacks) or one or more antennas to connect to the communications network 1681.

By way of example, the network interface device 1688 may include a plurality of antennas to communicate wirelessly using at least one of a single-input multiple-output ("SIMO"), or a multiple-input single output ("MISO") methods. The phrase, "transmission medium" includes any intangible medium that is capable of storing, encoding, or carrying instructions for execution by the computational machine 1600, and includes analog or digital communications signals or other intangible medium to facilitate communication of such software.

Exemplary methods in accordance with this disclosure may be machine or computer-implemented at least in part. Some examples may include a computer-readable medium or machine-readable medium encoded with instructions operable to configure an electronic device to perform the exemplary methods described herein. An example implementation of such an exemplary method may include code, such as assembly language code, microcode, a higher-level language code, or other code. Such code may include computer readable instructions for performing various methods. The code may form portions of computer program products. Further, in an example, the code may be tangibly stored on or in a volatile, non-transitory, or non-volatile tangible computer-readable media, such as during execution or other times. Examples of these tangible computer-readable media may include, but are not limited to, removable optical discs (e.g., compact discs and digital video discs), hard drives, removable magnetic discs, memory cards or sticks, include removable flash storage drives, magnetic cassettes, random access memories (RAMs), read only memories (ROMS), and other media.

There are a variety of methods to generate a 3D model from 2D preoperative or intraoperative images. By way of example, one such method may comprise receiving a set of 2D radiographic images of an operative area 170 of a patient with a radiographic imaging system, computing a first 3D model using epipolar geometry principles with a coordinate system of the radiographic imaging system and projective geometry data from the respective 2D images (see FIGS. 4 and 5A and 5B). Such an exemplary method may further comprise projecting the first 3D model on the 2D radiographic images and then adjusting the initial 3D model by registering the first and second radiographic images 30, 50 on the first 3D model with an image-to-image registration technique. Once the image-to-image registration technique has been applied, a revised 3D model may be generated. This process can repeat until the desired clarity in achieved.

By way of another example, a deep learning network (also known as a "deep neural network" ("DNN"), such as a convolutional neural network ("CNN"), recurrent neural network ("RNN"), modular neural network, or sequence to sequence model, can be used to generate a 3D model of the subject orthopedic element 1100 and/or a 3D model of the patient-specific surgical guide 500 from a set of at least two 2D images of an operative area 170 of a patient. The 2D images 30, 50 are desirably tissue penetrating images, such as radiographic images (e.g., X-ray or fluoroscopy images). In such a method, the deep learning network can generate a model from the projective geometry data (i.e., spatial data 43 or volume data 75) from the respective 2D images. The deep learning network can have the advantage of being able to generate a mask of the different subject orthopedic elements 100 (e.g., bones, soft tissues, etc.) in the operative area 170 as well as being able to calculate a volume (see 61, FIG. 6) of one or more imaged orthopedic elements 100.

Figure 8:
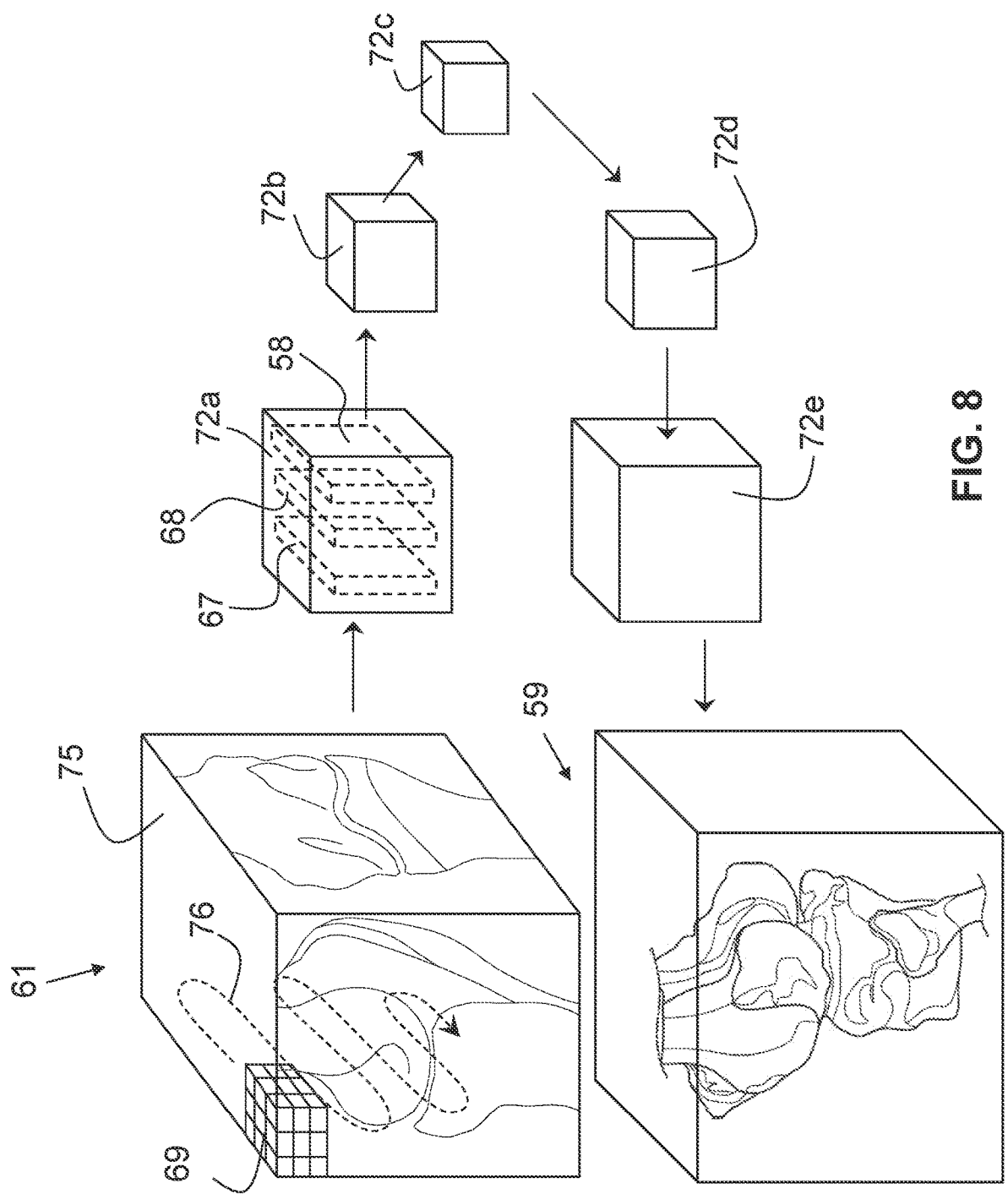
FIG. 8 is a schematic representation depicting how a CNN type deep learning network can be used to identify features (e.g., anatomical landmarks), including the surface of a subject orthopedic element.

FIG. 8 is a schematic representation of a CNN that illustrates how the CNN can be used to identify the surface topography of a subject orthopedic element 100. Without being bound by theory, it is contemplated that a CNN may be desirable for reducing the size of the volume data 75 without losing features that are necessary to identify the desired orthopedic element 100 or the desired surface topography. The volume data 75 of the multiple back projected input images 30, 50 is a multidimensional array that can be known as an "input tensor." This input tensor comprises the input data (which is the volume data 75 in this example) for the first convolution. A filter (also known as a kernel 69) is shown disposed in the volume data 75. The kernel 69 is a tensor (i.e., a multi-dimensional array) that defines a filter or function (this filter or function is sometimes known as the "weight" given to the kernel). In the depicted embodiment, the kernel tensor 69 is three dimensional. The filter or function that comprises the kernel 69 can be programed manually or learned through the CNN, RNN, or other deep learning network. In the depicted embodiment, the kernel 69 is a 3×3×3 tensor although all tensor sizes and dimensions are considered to be within the scope of this disclosure, provided that the kernel tensor size is less than the size of the input tensor.

Each cell or voxel of the kernel 69 has a numerical value. These values define the filter or function of the kernel 69. A convolution or cross-correlation operation is performed between the two tensors. In FIG. 8, the convolution is represented by the path 76. The path 76 that the kernel 69 follows is a visualization of a mathematical operation. Following this path 76, the kernel 69 eventually and sequentially traverses the entire volume 61 of the input tensor (e.g., the volume data 75). The goal of this operation is to extract features from the input tensor.

Convolution layers 72 typically comprise one or more of the following operations: a convolution stage 67, a detector stage 68, and a pooling stage 58. Although these respective operations are represented visually in the first convolution layer 72a in FIG. 8, it will be appreciated that the subsequent convolution layers 72b, 72c, etc. may also comprise one or more or all of the convolution stage 67, detector stage 68, and pooling layer 58 operations or combinations or permutations thereof. Furthermore, although FIG. 8, depicts five convolution layers 72a, 72b, 72c, 72d, 72e of various resolutions, it will be appreciated that more or less convolution layers may be used in other exemplary embodiments.

In the convolution stage 67, the kernel 69 is sequentially multiplied by multiple patches of pixels in the input data (i.e., the volume data 75 in the depicted example). The patch of pixels extracted from the data is known as the receptive field. The multiplication of the kernel 69 and the receptive field comprises an element-wise multiplication between each pixel of the receptive field and the kernel 69. After multiplication, the results are summed to form one element of a convolution output. This kernel 69 then shifts to the adjacent receptive field and the element-wise multiplication operation and summation continue until all the pixels of the input tensor have been subjected to the operation.

Until this stage, the input data (e.g., the volume data 75) of the input tensor has been linear. To introduce non-linearity to this data, a nonlinear activation function is then employed. Use of such a non-linear function marks the beginning of the detector stage 68. A common non-linear activation function is the Rectified Linear Unit function ("ReLU"), which is given by the function:

$$\mathrm{Re}LU(x) = \begin{Bmatrix} 0, \text{ if } & x < 0 \\ x, \text{ if } & x \geq 0 \end{Bmatrix}$$

When used with bias, the non-linear activation function serves as a threshold for detecting the presence of the feature extracted by the kernel 69. For example, applying a convolution or a cross-correlation operation between the input tensor and the kernel 69, wherein the kernel 69 comprises a low level edge filter in the convolution stage 67 produces a convolution output tensor. Then, applying a non-linear activation function with a bias to the convolution output tensor will return a feature map output tensor. The bias is sequentially added to each cell of the convolution output tensor. For a given cell, if the sum is greater than or equal to 0 (assuming ReLU is used in this example), then the sum will be returned in the corresponding cell of the feature map output tensor. Likewise, if the sum is less than 0 for a given cell, then the corresponding cell of the feature map output tensor will be set to 0. Therefore, applying non-linear activations functions to the convolution output behaves like a threshold for determining whether and how closely the convolution output matches the given filter of the kernel 69. In this manner, the non-linear activation function detects the presence of the desired features from the input data (e.g., the volume data 75 in this example).

All non-linear activation functions are considered to be within the scope of this disclosure. Other examples include the Sigmoid, TanH, Leaky ReLU, parametric ReLU, Softmax, and Switch activation functions.

However, a shortcoming of this approach is that the feature map output of this first convolutional layer 72a records the precise position of the desired feature (in the above example, an edge). As such, small movements of the feature in the input data will result in a different feature map. To address this problem and to reduce computational power, down sampling is used to lower the resolution of the input data while still preserving the significant structural elements. Down sampling can be achieved by changing the stride of the convolution along the input tensor. Down sampling is also achieved by using a pooling layer 58.

Valid padding may be applied to reduce the dimensions of the convolved tensor (see 72b) compared to the input tensor (see 72a). A pooling layer 58 is desirably applied to reduce the spatial size of the convolved data, which decreases the computational power required to process the data. Common pooling techniques, including max pooling and average pooling may be used. Max pooling returns the maximum value of the portion of the input tensor covered by the kernel 69, whereas average pooling returns the average of all the values of the portion of the input tensor covered by the kernel 69. Max pooling can be used to reduce image noise.

In certain exemplary embodiments, a fully connected layer can be added after the final convolution layer 72e to learn the non-linear combinations of the high level features (such as the profile of an imaged proximal tibia 110 or the surface topology of the orthopedic element) represented by the output of the convolutional layers.

The top half of FIG. 8 represents compression of the input volume data 75, whereas the bottom half represents decompression until the original size of the input volume data 75 is reached. The output feature map of each convolution layer 72a, 72b, 72c, etc. is used as the input for the following convolution layer 72b, 72c, etc. to enable progressively more complex feature extraction. For example, the first kernel 69 may detect edges, a kernel in the first convolution layer 72b may detect a collection of edges in a desired orientation, a kernel in a third convolution layer 72c may detect a longer collection of edges in a desired orientation, etc. This process may continue until the entire profile of the medial distal femoral condyle is detected by a downstream convolution layer 72.

The bottom half of FIG. 8 up-samples (i.e., expands the spatial support of the lower resolution feature maps. A de-convolution operation is performed in order to increase the size of the input for the next downstream convolutional layer (see 72c, 72d, 72e). For the final convolution layer 72e, a convolution can be employed with a 1×1×1 kernel 69 to produce a multi-channel output volume 59 that is the same size as the input volume 61. Each channel of the multi-channel output volume 59 can represent a desired extracted high level feature. This can be followed by a Softmax activation function to detect the desired orthopedic elements 100. For example, the depicted embodiment may comprise six output channels numbered 0, 1, 2, 3, 4, 5 wherein channel 0 represents identified background volume, channel 1 represents the identified distal femur 105, channel 2 represents the identified proximal tibia 110, channel 3 represents the identified proximal fibula 111, channel 4 represents the identified patella 901, and channel 5 represents the identified surface topography of a subject orthopedic element 100.

In exemplary embodiments, select output channels comprising output volume data 59 of the desired orthopedic element 100 can be used to create a 3D model of the subject orthopedic element 1100. For example, data from the channel representing the identified surface topography of the subject orthopedic element 100 can be mapped and reproduced as one or more mating surfaces (see 40 and 36 in FIGS. 11 and 53 and 54 in FIG. 12) on the patient-specific surgical guide 500 to create a patient-specific surgical guide 500 that is configured to be securely engaged to the subject orthopedic element 100. Producing a physical patient-specific surgical guide 500 via a manufacturing technique and sterilizing said patient-specific surgical guide 500 can permit the surgeon to install and use the patient-specific surgical guide 500 directly in the operative area 170. In this manner, the patient-specific surgical guide 500 can be said to be "configured to abut" the orthopedic element 100 on the identified surface. Likewise, in this manner, a computational machine 1600 that uses a deep learning network in this or a related manner to isolate individual orthopedic elements 100 or portions of orthopedic elements (e.g., a surface topography of a subject orthopedic element 100) can be said to be "configured to identify" a surface topography on the actual subject orthopedic element 100 or on a 3D model of the subject orthopedic element 1100 to define an identified surface.

Although the above example described the use of a three dimensional tensor kernel 69 to convolve the input volume data 75, it will be appreciated that the general model described above can be used with 2D spatial data 43 from the first calibrated input image 30 and the second calibrated input image 50 respectively. In other exemplary embodiments, a machine learning algorithm (i.e., a deep learning network (such as for example, a CNN)) can be used after calibration of the imaging machine but before 2D to 3D reconstruction. That is, the CNN can be used to detect features (e.g., anatomical landmarks) of a subject orthopedic element 100 from the first reference frame 30*a* and the second reference frame 50*a* of the respective 2D input images 30, 50. In exemplary embodiments, CNN may be used to identify high level orthopedic elements (e.g., the distal femur 105 and a portion of the surface topology of the subject orthopedic element 100) from the 2D input images 30, 50. The CNN may then optionally apply a mask or an outline to the detected orthopedic element 100 or surface topography of a subject orthopedic element 100. It is contemplated that if the imaging machine 1800 is calibrated and if the CNN identified multiple corresponding image points (e.g., $X_L$, $X_R$) of features between the two input images 30, 50, then the transformation matrices between the reference frames 30*a*, 50*a* of a subject orthopedic element 100 can be used to align the multiple corresponding image points in 3D space.

In certain exemplary embodiments that comprise using a deep learning network to add a mask or an outline to the detected 2D orthopedic element 100 from the respective input images 30, 50, only the 2D masks or outlines of the identified orthopedic element 100 or surface topography of the identified orthopedic element 100 can be sequentially back-projected in the manner described with reference to FIGS. 4 and 6 supra to define a volume 61 of the identified orthopedic element 100. In this exemplary manner, a 3D model of the subject orthopedic element 1100 may be created.

In embodiments wherein the first image 30 and the second image 50 are radiographic X-ray images, training a CNN can present several challenges. By way of comparison, CT scans typically produce a series of images of the desired volume. Each CT image that comprises a typical CT scan can be imagined as a segment of the imaged volume. From these segments, a 3D model can be created relatively easily by adding the area of the desired element as the element is depicted in each successive CT image. The modeled element can then be compared with the data in the CT scan to ensure accuracy.

By contrast, radiographic imaging systems typically do not generate sequential images that capture different segments of the imaged volume; rather, all of the information of the image is flattened on the 2D plane. Additionally, because a single radiographic image 30 inherently lacks 3D data, it is difficult to check the model generated by the epipolar geometry reconstruction technique described above with the actual geometry of the target orthopedic element 100. To address this issue, the CNN can be trained with CT images, such as digitally reconstructed radiograph ("DRRs") images. By training the deep learning network in this way, the deep learning network can develop its own weights (e.g., filters) for the kernels 69 to identify a desired orthopedic element 100 or surface topography of a subject orthopedic element 100. Because X-ray radiographs have a different appearance than DRRs, image-to-image translation can be performed to render the input X-ray images to have a DRR-style appearance. An example image-to-image translation method is the Cycle-GAN image translation technique. In embodiments in which image-to-image style transfer methods are used, the style transfer method is desirably used prior to imputing the data into a deep learning network for feature detection.

The above examples are provided for illustrative purposes and are in no way intended to limit the scope of this disclosure. All methods for generating a 3D model of the subject orthopedic element 1100 from 2D radiographic images of the same subject orthopedic element 100 taken from at least two transverse positions (e.g., 30*a*, 50*a*) are considered to be within the scope of this disclosure.

Figure 10:
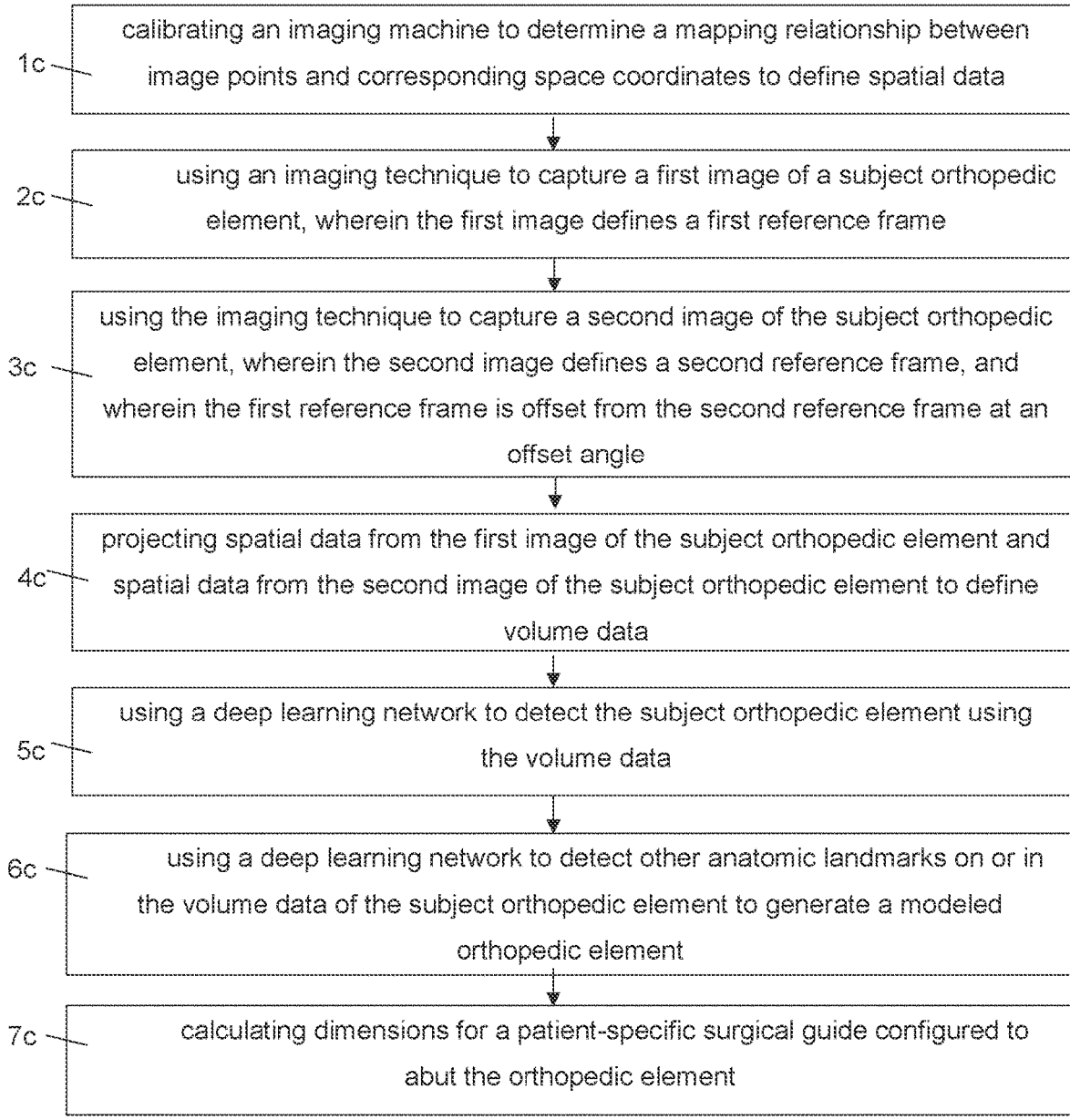
FIG. 10 is a flow chart depicting the steps of an exemplary method.

FIG. 10 is a flow chart that outlines the steps of an exemplary method that uses a deep learning network to calculate dimensions for a patient-specific surgical guide 500 to abut an orthopedic element 100 using two flattened input images (30, 50, FIGS. 4 and 5A and 5B) taken from an offset angle θ. The exemplary method comprises: step 1c calibrating an imaging machine 1800 (FIG. 9) to determine a mapping relationship between image points (see $X_L$, $e_L$, $X_R$, $e_R$, FIG. 4) and corresponding space coordinates (e.g., Cartesian coordinates on an x, y plane) to define spatial data 43. The imaging machine 1800 is desirably a radiographic imaging machine capable of producing X-ray images ("X-ray images" can be understood to include fluoroscopic images), but all medical imaging machines are considered to be within the scope of this disclosure.

Step 2c comprises capturing a first image 30 (FIG. 5A) of a subject orthopedic element 100 using the imaging technique (e.g., an X-ray imaging technique, a CT imaging technique, an MRI imaging technique, or an ultrasound imaging technique), wherein the first image 30 defines a first reference frame 30*a* (e.g., a first transverse position). In step 3c, a second image 50 (FIG. 5B) of the subject orthopedic element 100 is captured using the imaging technique, wherein the second image 50 defines a second reference frame 50*a* (e.g., a second transverse position), and wherein the first reference frame 30*a* is offset from the second reference frame 50*a* at an offset angle θ. The first image 30 and the second image 50 are input images from which data (including spatial data 43) can be extracted. It will be appreciated that in other exemplary embodiments, more than two images may be used. In such embodiments, each input image is desirably separated from the other input images by an offset angle θ. Step 4c comprises projecting spatial data 43 from the first image 30 of the subject orthopedic element 100 and the spatial data 43 from the second image 50 of the subject orthopedic element 100 to define volume data 75 (FIG. 6) using epipolar geometry.

Step 5c comprises using a deep learning network to detect the orthopedic element 100 from the volume data 75. Step 6c comprises using a deep learning network to detect other features (e.g., anatomical landmarks) from the volume data 75 of the subject orthopedic element 100 to define a 3D model of the subject orthopedic element 1100, including a surface topography of the subject orthopedic element 100. Step 7c comprises calculating dimensions for a patient-specific surgical guide 500. In such embodiments, the dimensions of a mating surface of the patient specific surgical guide 500 can be complementary to the surface topography of a portion of the subject orthopedic element 100. In this manner, the patient-specific surgical guide 500 can be configured to abut and be securely engaged to the orthopedic element 100.

In certain exemplary embodiments, the deep learning network that detects an anatomical landmark of the subject orthopedic element 100 from the volume data 75 can be the same deep learning network that detects other features from the volume data 75 of the subject orthopedic element 100, such as the surface topography of the subject orthopedic element. In other exemplary embodiments, the deep learning network that detects an anatomical landmark of the subject orthopedic element 100 from the volume data 75 can be different from the deep learning network that detects other feature from the volume data 75 of the subject orthopedic element 100, such as the surface topography of the subject orthopedic element.

In certain exemplary embodiments, the first image 30 can depict the subject orthopedic element 100 in a lateral transverse position (i.e., the first image 30 is a lateral view of the orthopedic element 100). In other exemplary embodiments, the second image 50 can depict the orthopedic element 100 in an anterior-posterior ("AP") transverse position (i.e., the second image 50 is an AP view of the orthopedic element 100). In yet other exemplary embodiments, the first image 30 can depict the orthopedic element 100 in an AP transverse position. In still other exemplary embodiments, the second image 50 can depict the orthopedic element 100 in a lateral transverse position. In still yet other exemplary embodiments, neither the first image 30 nor the second image 50 can depict the orthopedic element 100 in an AP transverse position or a lateral transverse position, provided that the first image 30 is offset from the second image 50 by an offset angle θ. The computational machine 1600 can calculate the offset angle θ from input images 30, 50 that include the calibration jig (see 973, FIG. 5A and 5B). The first image 30 and second image 50 may be referred to collectively as "input images" or individually as an "input image." These input images 30, 50 desirably depict the same subject orthopedic element 100 from different angles. These input images 30, 50 can be taken along a transverse plane of the subject orthopedic element 100.

Certain exemplary systems or methods can further comprise using a style transfer deep learning network such as Cycle-GAN. Systems or methods that use a style transfer deep learning network may start with a radiographic input image (e.g., 30) and use the style transfer deep learning network to transfer the style of the input image to a DRR type image. Yet further exemplary methods may comprise using a deep learning network to identify features (e.g., anatomical landmarks) of the subject orthopedic element 100 (which can include a portion of the surface topology of the subject orthopedic element 100) to provide a segmentation mask for each subject orthopedic element 100.

Without being bound by theory, it is contemplated that embodiments that utilize radiographic input images may be able to provide smoother surface on the 3D model of the orthopedic element compared to 3D models produced from CT input images or MRI input images. CT scans typically scan the subject orthopedic element at 1 mm increments. The change in surface topography between a first CT segment scan and an adjacent CT segment scan can result in a loss of information in the output of a traditional CT system because surface topographic details that are spaced less than 1 mm apart are not captured by a CT system that incrementally scans a subject orthopedic element in 1 mm increments. As a result, technicians typically had to manually smooth out the surface topography of a CT 3D model in order to create a surgical guide that was able to mate with the actual subject orthopedic element intraoperatively. Because topographic data less than 1 mm of the actual subject orthopedic element was never captured, this manual smoothing process tended to be imprecise and could result in a less than perfect fit. Certain embodiment in accordance with the present disclosure can obviate this problem because the radiographic X-ray images can be expressed as an array of pixel values. Pixel density varies, but by way of example, if the first and second input images have a resolution of 96 dots per inch ("dpi") (a unit of pixel density), then there are 25.4 mm in that inch, or 3.78 pixels per millimeter. Stated differently, there are an extra 3.78 pixels of information per millimeter in this example compared to a traditional CT scan. Higher pixel densities will likewise result in an even greater resolution of the surface topography, while the use of the deep learning network(s) as described herein can reduce the computational load of the computational machine compared to systems and methods that do not use a deep learning network.

It is further contemplated that in certain exemplary embodiments, the exemplary systems and/or methods can take surgeon input and preferences into account. For example, if the surgeon desires to orient the distal resection plane of the distal femur at three degrees varus, an exemplary patient-specific femoral resection guide mount 500a can be produced in accordance with this disclosure and the resection slot 52 can be manufactured relative to the body 42 such that the resection slot 52 is oriented at three degrees varus when the patient-specific surgical guide 500 is installed on the distal femur 105. The orientation of the resection slot 52 can be further modified in exemplary embodiments to accommodate limited access or obstructions to the operative area 170, which can be common in minimally invasive procedures.

An exemplary method for generating patient-specific surgical guides comprises: calibrating a radiographic imaging machine to determine a mapping relationship between image points and corresponding space coordinates to define spatial data; capturing a first image of an orthopedic element using a radiographic imaging technique, wherein the first image defines a first reference frame; capturing a second image of the orthopedic element using the radiographic imaging technique, wherein the second image defines a second reference frame, and wherein the first reference frame is offset from the second reference frame at an offset angle; using a deep learning network to detect the orthopedic element using the spatial data, the spatial data defining anatomical landmarks on or in the orthopedic element; using the deep learning network to apply a mask to the orthopedic element defined by an anatomical landmark; projecting the spatial data from the first image of the desired orthopedic element and the spatial data from the second image of the desired orthopedic element to define volume data, wherein the spatial data comprising image points disposed within a masked area of either the first image or the second image have a first value and wherein the spatial data comprising image points disposed outside of the masked area of either the first image or the second image have a second value, wherein the first value is different from the second value; applying the deep learning network to the volume data to generate a reconstructed 3D model of the orthopedic element; and calculating dimensions for a patient-specific surgical guide configured to abut the orthopedic element.

An exemplary method for generating patient-specific surgical guide comprises: calibrating a radiographic imaging machine to determine a mapping relationship between image points and corresponding space coordinates to define spatial data; using a radiographic imaging technique to capture a first image of an orthopedic element, wherein the first image defines a first reference frame; using the radiographic imaging technique to capture a second image of the orthopedic element, wherein the second image defines a second reference frame, and wherein the first reference frame is offset from the second reference frame at an offset angle; using a deep learning network to detect the orthopedic element using the spatial data, the spatial data defining an anatomical landmark on or in the orthopedic element; using the deep learning network to apply a mask to the orthopedic element defined by the anatomical landmark; projecting the spatial data from the first image of the desired orthopedic element and the spatial data from the second image of the desired orthopedic element to define volume data, wherein the spatial data comprising image points disposed within a masked area of either the first image or the second image have a positive value and wherein the spatial data comprising image points disposed outside of a masked area of either the first image or the second image have a negative value; applying the deep learning network to the volume data to generate a 3D model of the orthopedic element; and calculating dimensions for a patient-specific surgical guide configured to be securely engaged to the orthopedic element.

In an exemplary embodiment, the method further comprises using the deep learning network to perform a style transfer on the first image and the second image.

In an exemplary embodiment, the style transfer converts the spatial data from the radiographic imaging technique into dynamic digital radiography data.

In an exemplary embodiment, the first value is a positive value.

In an exemplary embodiment, the second value is a negative value.

In an exemplary embodiment, the method further comprises projecting the reconstructed 3D model on a display.

In an exemplary embodiment, the deep learning network comprises a deep learning algorithm.

An exemplary system comprises: a 3D model of an orthopedic element comprising an operative area generated from at least two 2D radiographic images, wherein at least a first radiographic image is captured at a first position, and wherein at least a second radiographic image is captured at a second position, and wherein the first position is different than the second position; a computational machine configured to identify a surface topography on the 3D model of the orthopedic element to define an identified surface and further configured to calculate dimensions for a patient-specific surgical guide configured to abut the orthopedic element on the identified surface.

An exemplary system can further comprise a display, wherein the 3D model of the orthopedic element is displayed on the display. In an exemplary system, the display can be an augmented reality device or a virtual reality device. An exemplary system can further comprise an X-ray imaging machine.

An exemplary system can further comprise a manufacturing device, wherein the manufacturing device is configured to produce a physical model of a patient-specific surgical guide.

In an exemplary system comprising a manufacturing device, the manufacturing device can be configured to produce at least a partial physical model of the identified surface of the orthopedic element. The manufacturing device can be an additive manufacturing device.

In an exemplary system the physical model of the patient-specific surgical guide can comprise a medical grade polyamide.

An patient-specific surgical guide produced by an exemplary process can comprise: calibrating a radiographic imaging machine to determine a mapping relationship between radiographic image points and corresponding space coordinates to define spatial data; using a radiographic imaging technique to capture a first radiographic image of a subject orthopedic element, wherein the first radiographic image defines a first reference frame; using the radiographic imaging technique to capture a second radiographic image of the subject orthopedic element, wherein the second radiographic image defines a second reference frame, and wherein the first reference frame is offset from the second reference frame at an offset angle; projecting spatial data from the first radiographic image of the subject orthopedic element and spatial data from the second radiographic image of the subject orthopedic element to define volume data; using a deep learning network to detect the subject orthopedic element using the volume data, the volume data defining an anatomical landmark on or in the subject orthopedic element; using the deep learning network to identify a surface on an orthopedic element to define an identified surface using the volume data; and applying the deep learning network to the volume data to calculate dimensions for a patient-specific surgical guide configured to abut the orthopedic element on the identified surface.

An exemplary product by process can further comprise using a manufacturing technique to produce a physical 3D model of the patient-specific surgical guide. In such embodiments, the physical 3D model of the patient-specific surgical guide can comprise a mating surface that mates with the identified surface on the orthopedic element.

For an exemplary product by process, the physical 3D model of the patient-specific surgical guide can comprise a mating surface, and the mating surface can further comprise a projection.

An exemplary patient-specific surgical guide can be produced by an exemplary process comprising: calibrating a radiographic imaging machine to determine a mapping relationship between radiographic image points and corresponding space coordinates to define spatial data; using a radiographic imaging technique to capture a first radiographic image of a subject orthopedic element, wherein the first radiographic image defines a first reference frame; using the radiographic imaging technique to capture a second radiographic image of the subject orthopedic element, wherein the second radiographic image defines a second reference frame, and wherein the first reference frame is offset from the second reference frame at an offset angle; projecting spatial data from the first radiographic image of the subject orthopedic element and spatial data from the second radiographic image of the subject orthopedic element; using a deep learning network to detect the subject orthopedic element using the spatial data, the spatial data defining an anatomical landmark on or in the subject orthopedic element; using the deep learning network to detect identify a surface on an orthopedic element to define an identified surface using the spatial data; and applying the deep learning network to the spatial data to calculate dimensions for a patient-specific surgical guide configured to abut the orthopedic element on the identified surface.

It is to be understood that the present invention is by no means limited to the particular constructions and method steps herein disclosed or shown in the drawings, but also comprises any modifications or equivalents within the scope of the claims known in the art. It will be appreciated by those skilled in the art that the devices and methods herein disclosed will find utility.

What is claimed is:
1. A system comprising:
 a radiographic imaging machine, the radiographic imaging machine being calibrated to determine a mapping relationship between radiographic image points and corresponding space coordinates to define spatial data;

a first radiographic image of a subject orthopedic element, the first radiographic image captured by the radiographic imaging machine, wherein the first radiographic image defines a first reference frame;

a second radiographic image of the subject orthopedic element, the second radiographic image captured by the radiographic imaging machine, wherein the second radiographic image defines a second reference frame, wherein the first reference frame is offset from the second reference frame at an offset angle; and a computational machine, wherein the computational machine receives the first radiographic image and the second radiographic image, wherein the computational machine projects spatial data form the first radiographic image and the second radiographic image along the offset angle to define volume data, wherein the computational machine uses a deep learning network to identify a surface of the subject orthopedic element using the volume data to define an identified surface, and wherein the computational machine further outputs a mating surface of a patient-specific surgical guide using the identified surface.

2. The system of claim 1, further comprising a display, wherein the display displays an image selected from the group consisting essentially of: a 3D model of the subject orthopedic element, a 3D model of a patient-specific surgical guide, the identified surface, and the mating surface.

3. The system of claim 2, wherein the display is an augmented reality device or a virtual reality device.

4. The system of claim 1 further comprising a manufacturing device, wherein the manufacturing device is configured to produce the patient-specific surgical guide.

5. The system of claim 4, wherein the manufacturing device is configured to produce at least a partial physical model of the identified surface of the orthopedic element.

6. The system of claim 4, wherein the manufacturing device is an additive manufacturing device.

7. The system of claim 4, wherein the patient-specific surgical guide comprises a medical grade polyamide.

8. The system of claim 4, wherein the mating surface of the patient-specific surgical guide further comprises a projection.

* * * * *